United States Patent
Dietz et al.

(10) Patent No.: US 11,771,703 B2
(45) Date of Patent: Oct. 3, 2023

(54) TARGETED EPIGENETIC THERAPY AGAINST DISTAL REGULATORY ELEMENT OF TGFβ2 EXPRESSION

(71) Applicant: The Johns Hopkins University, Baltimore, MD (US)

(72) Inventors: Harry C. Dietz, Towson, MD (US); Joseph Shin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 247 days.

(21) Appl. No.: 16/495,098

(22) PCT Filed: Mar. 16, 2018

(86) PCT No.: PCT/US2018/022984
§ 371 (c)(1),
(2) Date: Sep. 17, 2019

(87) PCT Pub. No.: WO2018/170464
PCT Pub. Date: Sep. 20, 2018

(65) Prior Publication Data
US 2021/0275541 A1 Sep. 9, 2021

Related U.S. Application Data

(60) Provisional application No. 62/624,024, filed on Jan. 30, 2018, provisional application No. 62/532,525, filed on Jul. 14, 2017, provisional application No. 62/472,955, filed on Mar. 17, 2017.

(51) Int. Cl.
*A61K 31/551* (2006.01)
*A61K 38/55* (2006.01)

(52) U.S. Cl.
CPC ............ *A61K 31/551* (2013.01); *A61K 38/55* (2013.01)

(58) Field of Classification Search
CPC .................................................. A61K 31/551
See application file for complete search history.

(56) References Cited

U.S. PATENT DOCUMENTS

| | | |
|---|---|---|
| 4,391,904 A | 7/1983 | Litman et al. |
| 5,283,173 A | 2/1994 | Fields et al. |
| 5,288,514 A | 2/1994 | Ellman |
| 5,468,614 A | 11/1995 | Fields et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,490 A | 6/1996 | Erickson et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,593,853 A | 1/1997 | Chen et al. |
| 5,605,662 A | 2/1997 | Heller et al. |
| 5,637,463 A | 6/1997 | Dalton et al. |
| 5,667,973 A | 9/1997 | Fields et al. |
| 8,309,700 B2 | 11/2012 | Mizutani |
| 8,697,359 B1 | 4/2014 | Zhang |
| 2002/0193284 A1 | 12/2002 | Chen |
| 2007/0207965 A1 | 9/2007 | Cuesta |
| 2013/0001467 A1 | 1/2013 | Auner et al. |
| 2013/0071467 A1* | 3/2013 | Niitsu .................... A61P 43/00 424/450 |
| 2013/0142887 A1* | 6/2013 | Alani .................... C12Q 1/025 424/649 |
| 2015/0232883 A1 | 8/2015 | Dahlman et al. |
| 2016/0040167 A1 | 2/2016 | Jaschinski et al. |
| 2016/0235716 A1 | 8/2016 | Kesicki et al. |
| 2016/0237490 A1* | 8/2016 | Hnisz .................... C12N 15/85 |

FOREIGN PATENT DOCUMENTS

| | | |
|---|---|---|
| WO | 8403564 | 9/1984 |
| WO | 9119735 | 12/1991 |
| WO | 9200091 | 1/1992 |
| WO | 9320242 | 10/1993 |
| WO | 9525116 | 9/1995 |
| WO | 9535505 | 12/1995 |
| WO | 2010090723 A2 | 8/2010 |
| WO | 2014197748 A2 | 12/2014 |
| WO | 2015015318 A2 | 2/2015 |
| WO | 2016/044777 A1 | 3/2016 |
| WO | 2016044777 A1 | 3/2016 |
| WO | 2016/123054 A2 | 8/2016 |
| WO | 2016/130600 A2 | 8/2016 |

(Continued)

OTHER PUBLICATIONS

Attisano Cancer and Metastasis Reviews 23: 53-61, 2004.*
Miao, International Immunopharmacology, vol. 28, Issue 1, Sep. 2015, pp. 626-633.*
Ghosh, Journal of Investigative Dermatology (2013) 133, 1302-1310.*
Altorok, Rheumatology 2015;54:17591770.*
Ikushima et al. "Autocrine TGF-b Signaling Maintains Tumorigenicity of Glioma-Initiating Cells through Sru-Related HMG-Box Factors," Cell Press, (Nov. 6, 2009), vol. 5, Iss. 5, pp. 504-514, entire document.
Mayanil et al. "Regulation of Murine TGFbeta2 by Pax3 during Eady Embryonic Development," The Journal of Biological Chemistry, (Jun. 19, 2006), vol. 281, No. 34, pp. 24544-24552, entire document.
Han et al. "TFGβ signaling and its targeting for glioma treatment," American Journal of Cancer Research, (Mar. 1, 2015), vol. 5, No. 3, pp. 945-955, entire document.

(Continued)

*Primary Examiner* — Nizal S Chandrakumar
(74) *Attorney, Agent, or Firm* — Fox Rothschild LLP

(57) ABSTRACT

The instant disclosure provides methods and compositions for the diagnosis, treatment and prevention of a TGFβ2-associated disease, disorder and/or condition, including, e.g., Scleroderma, other fibrotic disease, grade 4 glioblastoma (GBM) and/or Primary Open-Angle Glaucoma (POAG). The disclosure further provides pharmaceutical compositions and kits for the diagnosis, treatment and prevention of TGFβ2-associated diseases, disorders and/or conditions.

12 Claims, 21 Drawing Sheets

(56) References Cited

FOREIGN PATENT DOCUMENTS

| WO | 2016123054 A2 | 8/2016 |
|---|---|---|
| WO | 2016130600 A2 | 8/2016 |

OTHER PUBLICATIONS

Xu et al., "Empower multiplex cell and tissue-specific CRISPR-mediated gene manipulation with self-cleaving ribozymes and tRNA," Nucleic Acids Research, (Oct. 30, 2016), vol. 45, No. 5, e28, pp. 1-9, entire document.
International Search Report dated Jun. 8, 2018 for related International Application No. PCT/US2018/022984.
Shah AA and Wigley FM (2013). "My approach to the treatment of scledoderma." Mayo Clin Proc. 88: 377-393.
Radstake T et al. (2010). "Genome-wide association study of systemic sclerosis identifies CD247 as a new susceptibility locus." Nature. 42:426-432.
Murdaca G (2016). "Genetic factors and systemic sclerosis". Autoimmunity Reviews. 15:427-432).
Eguchi et al., 1991. "Antisense RNA." Ann. Rev. Biochem. 60, 631-652.
Sonnylal et al. "Postnatal Induction of Transforming Growth Factor Signaling in Fibroblasts of Mice Recapitulates Clinical, Histologic, and Biochemical Features of Scleroderma." Arthritis and Rheumatism 56:334-344.
Sfikakis et al. "Immunohistological Demonstration of Transforming Growth Factor-B Isoforms in the Skin of Patients with Systemic Sclerosis." Clinical Immunology and Immunopathology 69: 199-204.
Rodon et al. "Active CREB1 Promotes a Malignant TGFb2 Autocrine Loop in Glioblastoma." Cancer Discovery 4: 1230-41.
Fuchshofer et al. "The role of TGF-B in the pathogeniis of primary open-angle glaucoma." Cell Tissue Research 347:279-90.
Gerber, et al., "Integrin-modulating therapy prevents fibrosis and autoimmunity in mouse models of scleroderma." Nature 503: 126-130.
Murdaca, G. "Genetic factors and systemic sclerosis." Autoimmunity Reviews 15:427-432.
Feghali-Bostwick et al. "Analysis of Systemic Sclerosis in Twins Reveals Low Concordance for Disease and High Concordance for the Presence of Antinuclear Antibodies" Arthritis and Rheumatism 48: 1956-1963.
Birbair, et al. "Type-1 pericytes accumulate after tissue injury and produce collagen in an organ-dependent manner." Stem Cell Research & Therapy. 5 (6): 122.
Bleeker, et al. "Recent advances in the molecular understanding of glioblastoma." Journal of Neuro-Oncology. 108 (1): 11-27.
Young et al. "Current trends in the surgical management and treatment of adult glioblastoma". Annals of Translational Medicine 3 (9): 121.
Gallego, O. "Nonsurgical treatment of recurrent glioblastoma." Current oncology (Toronto, Ont.). 22 (4): e273-81.
Khosla, D. "Concurrent therapy to enhance radiotherapeutic outcomes in glioblastoma." Annals of translational medicine. 4 (3): 54.
Hart, MG, et al. "Temozolomide for high grade glioma (Review)." The Cochrane database of systematic reviews. 4: CD007415.
Van Meir et al. "Exciting New Advances in Neuro-Oncology" CA: A Cancer Journal for Clinicians. 60 (3): 166-93.
Mcneill, et al. Epidemiology of Brain Tumors. Neurologic Clinics. 34 (4): (981-998).
Mantravadi and Vadhar. "Glaucoma." Primary Care. Saunders (Elsevier). 42 (3): 437-49.
Mi et al. "The current research status of normal tension glaucoma." Clinical Interventions in Aging. 9: 1563-71.
Resnikoff et al. "Global data on visual impairment in the year 2002" Bulletin of the World Health Organization. 82 (11): 844-51.
Leffler et al. "What was Glaucoma Called Before the 20th Century?" Ophthalmology and Eye Diseases. Libertas Academica. 7: 21-33.
Schiffer "Targeted DNA Mutagenesis for the Cure of Chronic Viral Infections" 2012, J Viral 88(17):8920-8936.
Swarts D.C. et al. "The evolutionary journey of Argonaute proteins." The evolutionary journey of Argonaute proteins. Nat. Struct. Mal. Biol. 21, 743-753 (2014.
Makarova, K.S., et al. "Prokaryotic homologs of Argonaute proteins are predicted to function as key components of a novel system of defense against mobile genetic elements." Biol. Direct 4, 29 (2009).
Molloy, S. "Bacterial argonaute sets sail." Nat. Rev. Microbial. 11, 743 (2013).
Vogel, J. "A bacterial seek-and-destroy system for foreign DNA." Science 344, 972-973 (2014).
Swarts, D.C. et al. "DNA-guided DNA interference by a prokaryotic Argonaute." Nature 507, 258-261 (2014).
Olovnikov, I., et al. "Bacterial Argonaute Samples the Transcriptome to Identify Foreign DNA." Mal. Cell 51, 594-605 (2013).
Swarts D.C. et al. "Argonaute of the archaeon Pyrococcus furiosus is a DNA-guided nuclease that targets cognate DNA" Nucleic Acids Res. 43, 5120-5129 (2015).
Salomon, W.E., et al. "Single-Molecule Imaging Reveals that Argonaute Reshapes the Binding Properties of Its Nucleic Acid Guides." Cell 162, 84-95 (2015).
Jinek and Doudna. "Athree-dimensional view of the molecular machinery of RNA interference" (2009) Nature 457, 405-412).
Talia and Joshua-Tor. "Slicer and the Argonautes" (2007) Nat. Chem. Biol. 3, 36-3.
Drinnenberg et al., "RNAi in Budding Yeast." (2009) Science 326, 544-550.
Wang et al., "Structure of an argonaute silencing complex with a seed-containing guideDNA and target RNA duplex." (2008a) Nature 456, 921-926.
Wang Y. et al., "Distinct passenger strand and mRNA cleavage activities of human Argonaute proteins." (2009) Nat. Struct. Mal. Biol. 16, 1259-1266.
Wang et al., "Structure of the guide-strand-containing argonaute silencing complex." (2008b) Nature 456, 209-213).
Fields et al., "A novel genetic system to detect protein-protein interactins." Nature 340:245 (1989.
Vasavada et al., "A contingent replication assay for the detection of protein-protein interactions in animal cells". Proc. Nat'l Acad. Sci. USA 88: 10686 (1991).
Fearon et al., "Karyoplasmic interaction selection strategy: A general strategy to detect protein-protein interactions in mammalian cells" Proc. Nat'l Acad. Sci. USA 89:7958 (1992).
Dang et al., "Intracellular Leucine Zipper Interactions Suggest c-Myc Hetero-Oligomerization" Mol. Cell. Biol. 11:954 (1991).
Chien et al., "The two-hybrid system: A method to identify and clone genes for proteins that interact with a protein of interest" Proc. Nat'l Acad. Sci. USA 9578 (1991).
Schena et al., "Parallel human genome analysis: Microarray-based expression monitoring of 1000 genes" 1996, Proc. Natl. Acad. Sci. U.S.A. 93: 10614-10619.
Heller, et al., "Discovery and analysis of inflammatory disease-related genes using cDNA microarrays" 1997, Proc. Natl. Acad. Sci. U.S.A. 94: 2150-2155.
Merrifield J. "Solid Phase Peptide Synthesis. I. The Synthesis of a Tetrapeptide." Am. Chem. Soc. 85:2149-2154 (1963) (describing solid phase synthesis of, e.g., peptides.
Geysen et al., "Strategies for epitope analysis using peptide synthesis." J. Immun. Meth. 102:259-274 (1987) (describing synthesis of solid phase components on pins).
Frank & Doring. "Simultaneous Multiple Peptide Synthesis Under Continuous Flow Conditions on Cellulose Paper Discs as Segmental Solid Supports." Tetrahedron 44:60316040 ( 1988) (describing synthesis of various peptide sequences on cellulose disks).
Sheldon et al., "C-Reactive Protein and Its Cytokine Mediators in Intensive-Care Patients." Clinical Chemistry 39 (4):718-719 (1993).
Thompson et al., "Synthesis and Applications of Small Molecule Libraries" Synthesis and application of small molecule libraries, Chem Rev 96:555-600, 1996.

(56) References Cited

OTHER PUBLICATIONS

Global Burden of Disease Study 2013 Collaborators. Global, regional, and national incidence, prevalence, and years lived with disability for 301 acute and chronic diseases and injuries in 188 countries, 1990-2013: a systematic analysis for the Global Burden of Disease Study 2013. Lancet., (2015), 386 (9995), pp. 743-800.
Kleihues et al. Chapter 5.16: Tumors of the nervous system. World Cancer Report 2014., World Health Organization., (2014), pp. 511-521.
Savarese et al. Chapter 3.8: Signal Transduction and targeted therapy. World Cancer Report 2014., World Health Organization., (2014), pp. 244-251.
Southwick et al. Cyanine dye labeling reagents—carboxymethylindocyanine succinimidyl esters. Cytometry., (1990), 11 (3), pp. 418-430.
Ikushima et al. Autocrine TGF-beta signaling maintains tumorigenicity of glioma-initiating cells through Sry-related HMG-box factors. Cell Stem Cell., (2009), 5 (5), pp. 504-514.
Mayanil et al. Regulation of murine TGFbeta2 by Pax3 during early embryonic development. The Journal of Biological Chemistry., (2006), 281 (34), pp. 24544-24552.
Han et al. TGF-β signaling and its targeting for glioma treatment. American Journal of Cancer Research., (2015), 5 (3), pp. 945-955.
Xu et al. Empower multiplex cell and tissue-specific CRISPR-mediated gene manipulation with self-cleaving ribozymes and tRNA. Nucleic Acids Research., (2016), 45 (5), e28, pp. 1-9.
Hilton et al. Epigenome editing by a CRISPR-Cas9-based acetyltransferase activates genes from promoters and enhancers. Nature Biotechnology., (2015), 33 (5), pp. 510-517.
Aringer et al. Recent advances in managing systemic sclerosis. F1000Res., (2017), 6, 88.
Kungulovski et al. Epigenome editing: state of the art, concepts, and perspectives. Trends Genet., (2016), 32 (2), pp. 101-113.
Jaclyn Y. Bermudez et al: "HDAC Inhibitor-Mediated Epigenetic Regulation of Glaucoma-Associated TGF[beta]2 in the Trabecular Meshwork", Investigative Opthalmology & Visual Science, vol. 57, No. 8, Jul. 12, 2016 (Jul. 12, 2016), p. 3698.
Isaac B Hilton et al: "Epigenome editing by a CRISPR-Cas9-based acetyltransferase activates genes from promoters and enhancers", Nature Biotechnology, vol. 33, No. 5, Apr. 6, 2015 (Apr. 6, 2015), pp. 510-517.
Liyang Liu et al: "Association of tissue promoter methylation levels of APC, TGF-beta2, HOXD3 and RASSFIA with prostate cancer progression", International Journal of Cancer, vol. 129, No. 10, Jan. 4, 2011 (Jan. 4, 2011), pp. 2454-2462.
R. Sgonc et al: "Pro- and anti-fibrotic effects of TGF-beta in scleroderma", Rheumatology, vol. 47, No. Supplement 5, Sep. 10, 2008 (Sep. 10, 2008), pp. v5-v7.
Kopperuncholan Namachivayam et al: "Smad7 inhibits autocrine expression of TGF-[beta] 2 in intestinal epithelial cells in baboon necrotizing enterocolitis", American Journal of Physiology—Gastrointestinal and Liver Physiology, vol. 304, No. 2, Nov. 12, 2012 (Nov. 12, 2012), pp. G167-GI80.
Dhaouadi Nedra et al: "Computational identification of potential transcriptional regulators of TGF-BI in human atherosclerotic arteries", Genomics, Academic Press, San Diego, US. vol. 103, No. 5, May 10, 2014 (May 10, 2014), pp. 357-370.
Ralph Staohouders et al: Transcription regulation by distal enhancers : Who's in the loop? Tran Sc Ri Pt Ion, vol. 3, No. 4, Jul. 1, 2012 (Jul. 1, 2012), pp. 181-186.
Joseph Yusup Shin et al: "Epigenetic activation and memory at a TGFB2 enhancer in systemic sclerosis". Science Translational Medicine, vol. 11, No. 497, Jun. 19, 2019.
Supplementary European Search Report issued in EP 18768166 dated Dec. 3, 2020.
Kenan et al., "Exploring molecular diversity with combinatorial shape libraries." Exploring molecular diversity with combinatorial shape libraries, Trends Biochem Sci 19:57-64, 1994.
Janda. "Tagged versus untagged libraries: methods for the generation and screening of combinatorial chemical libraries", Proc NatlAcad Sci USA. 91:10779-85, 1994.
Lebl et al., "One-bead-one-structure combinatorial libraries," Biopolymers 37: 177-98, 1995.
Eichler et al., "Peptide, peptidomimetic, and organic synthetic combinatorial libraries," Med Res Rev. 15:481-96, 1995.
Chabala, et al. "Solid-phase combinatorial chemistry and novel tagging methods for identifying leads," Curr Opin Biotechnol. 6:632-9, 1995.
Dolle, et al. "Discovery of enzyme inhibitors through combinatorial chemistry," Mal Divers. 2:223-36, 1997.
Fauchere et al., "Peptide and nonpeptide lead discovery using robotically synthesized soluble libraries," Can J. Physiol Pharmacol. 75:683-9, 1997.
Eichler et al., "Generation and utilization of synthetic combinatorial libraries," Mal Med Today 1: 174-80, 1995.
Hobbs, et al., ""Diversomers": An approach to nonpeptide, nonoligomeric chemical diversity." Proc. Nat. Acad. Sci. USA, 90:6909-6913 (1993).
Hagihara, et al., "Vinylogous Polypeptides: An Alternative Peptide Backbone." J. Amer. Chem. Soc. 114:6568 (1992).
Hirschmann et al., "Nonpeptidal Peptidomimetics with a 8-D-Glucose Scaffolding. A Partial Somatostatin Agonist Bearing a Close Structural Relationship to a Potent, Selective Substance P Antagonist" J. Amer. Chem. Soc., 114:9217-9218 (1992).
Chen, et al., ""Analogous" Organic Synthesis of Small-Compound Libraries: Validation of Combinatorial Chemistry in Small-Molecule Synthesis" J. Amer. Chem. Soc., 116:2661 (1994).
Campbell et al., "Phosphonate Ester Synthesis Using a Modified Mitsunobu Condensation." J. Org. Chem. 59:658 (1994).
Vaughn et al., "Human Antibodies with Sub-Nanomolar Affinities Isolated from a Large Non-Immunized Phage Display Library." Nature Biotechnology, 14(3):309-314 (1996).
Barak et al., "A b-Arrestin/Green Fluorescent Protein Biosensor for Detecting G Protein-coupled Receptor Activation" (1997), J. Biol. Chem. 272:27497-27500.
Barber, et al. "Delivery of membrane-impermeant fluorescent probes into living neural cell populations by lipotransfer" (1996), Neuroscience Letters 207: 17-20.
Bright et al. "Delivery of Macromolecules Into Adherent Cells via Electroporation for Use in Fluorescence Spectroscopic Imaging and Metabolic Studies." (1996), Cytometry 24:226-233.
Cubitt et al. "Understanding, improving and using green fluorescent proteins." (1995), Trends in Biochemical Science 20:448-455.
Giulano et al. "Fluorescent Protein Biosensors: Measurement of Molecular Dynamics in Living Cells" (1995), Ann. Rev. of Biophysics and Biomolecular Structure 24:405-434.
Bright et al. "Fluorescense Ration Imaging Microscopy: Temporal and Spatial Measurements of Cytoplasmic pH." (1989), J. Cell Biology 104:1019-1033.
Thomas et al. "Intracellular pH Measurements in Ehrlich Ascites Tumor Cells Utilizing Spectroscopic Probes Generated in Situ" (1979), Biochemistry 18:2210-2218).
Buenrostro JC et al. "Transposition of native chromatin for fast and sensitive epigenomic profiling of open chromatin, DNDNA-binding proteins and nucleosome position" (2013). Nature Methods. IO: 1213-1218.
Calo E et al. "Modification of Enhancer Chromatin: What, How, and Why?" (2013). Cell Molecular Cell Reviews. 49:825-837.
Brown JD et al. "NF-kB directs dynamic super enhancer formation in inflammation and atherogenesis" (2014). Molecular Cell. 56:219-231.
Giuliano et al. "Determination of Intracellular pH of BALB/c-3T3 Cells Using the Fluorescence of Pyranine" (1987),Anal. Biochem. 167:362-371.
Kay et al., Identification of enzyme inhibitors from phage-displayed combinatorial peptide libraries, Comb Chem High Throughput Screen 4:535-43, 2001.
Liang et al., "Parallel Synthesis and Screening of a Solid Phase Carbohydrate Library." Science, 274: 1520-1522 (1996).
Fodor et al., "Light-directed, spatially addressable parallel chemical synthesis." Science, 251: 767-777 (1991).

(56) References Cited

OTHER PUBLICATIONS

Cho et al., "An Unnatural Polymer." Science, 261:1303 (1993).
Giuliano and Taylor. "Light-optical-based reagents for the measurement and manipulation of ions, metabolites, and macromolecules in living cells." (1995) Methods in Neuroscience 27: 1-16.
Tsien et al., "Chapter 5 Fluorescent Indicators of Ion Concentrations". Methods in Cell Biology, vol. 29 Taylor and Wang (eds.), pp. 127-156).
Kozal et al., "Extensive polymorphisms observed in HIV-1 clade B protease gene using high-density oligonucleotide arrays." Nature Medicine 2(7):753759 (1996).

* cited by examiner

FIGURE 1D – 1F
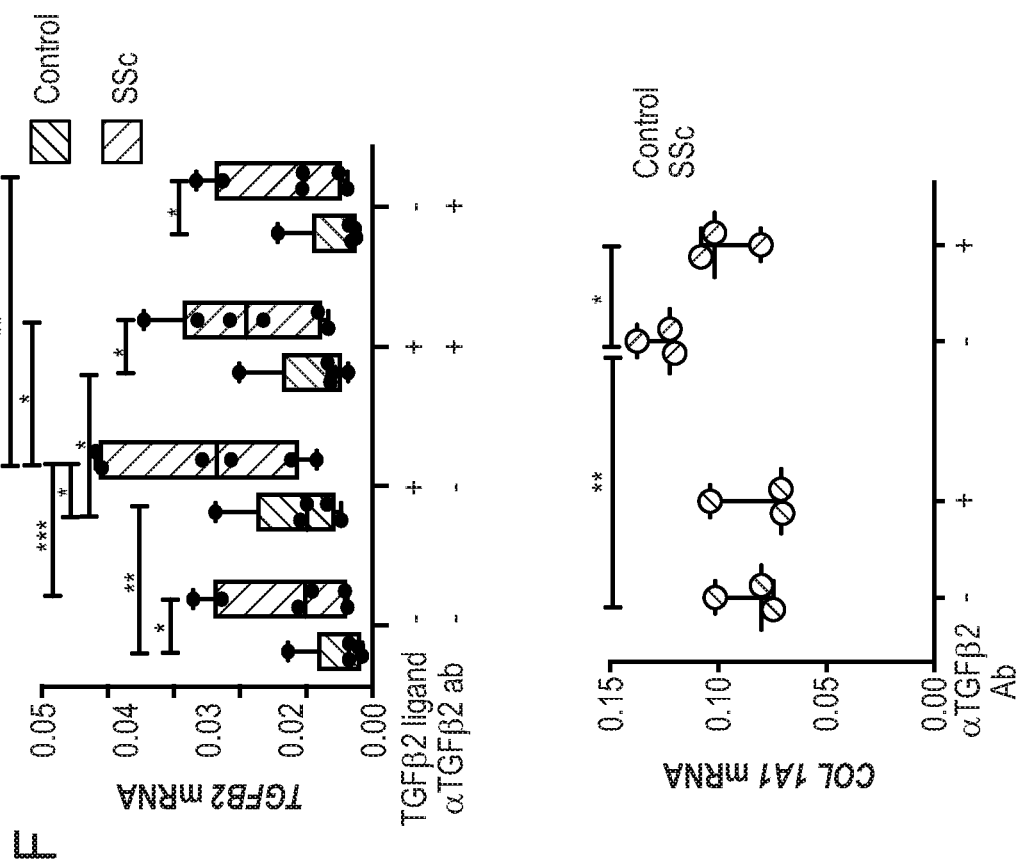
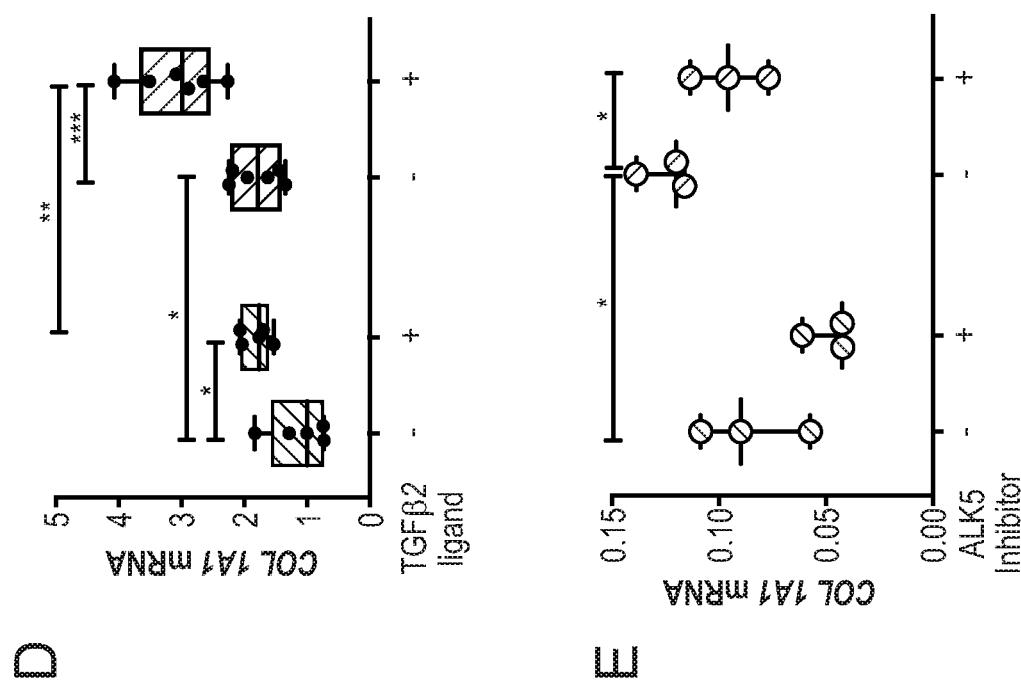

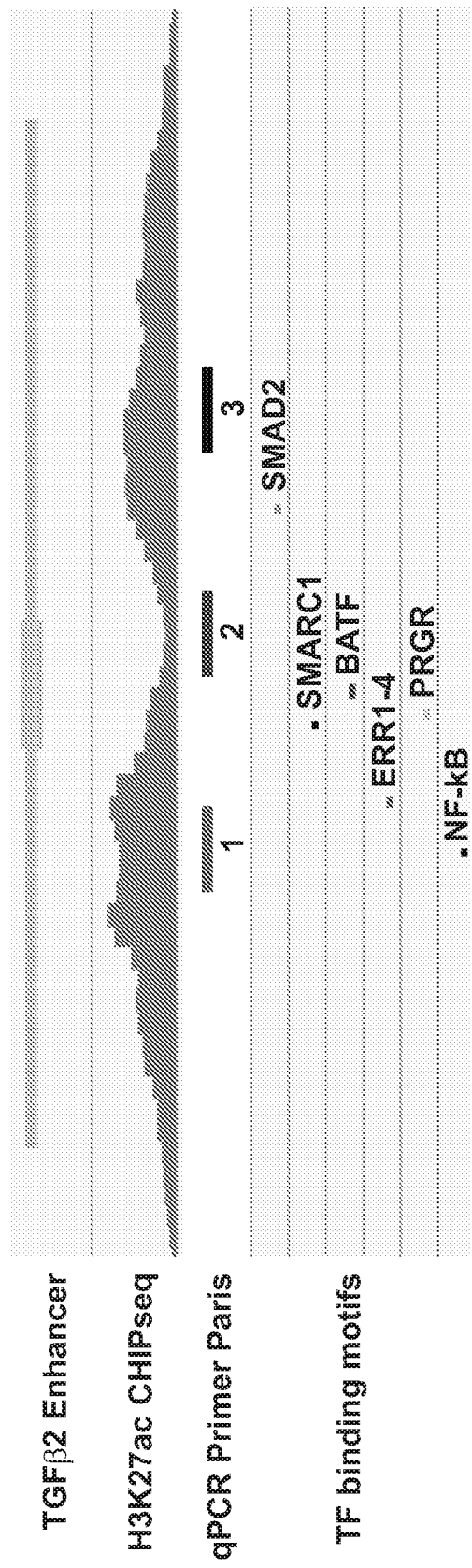

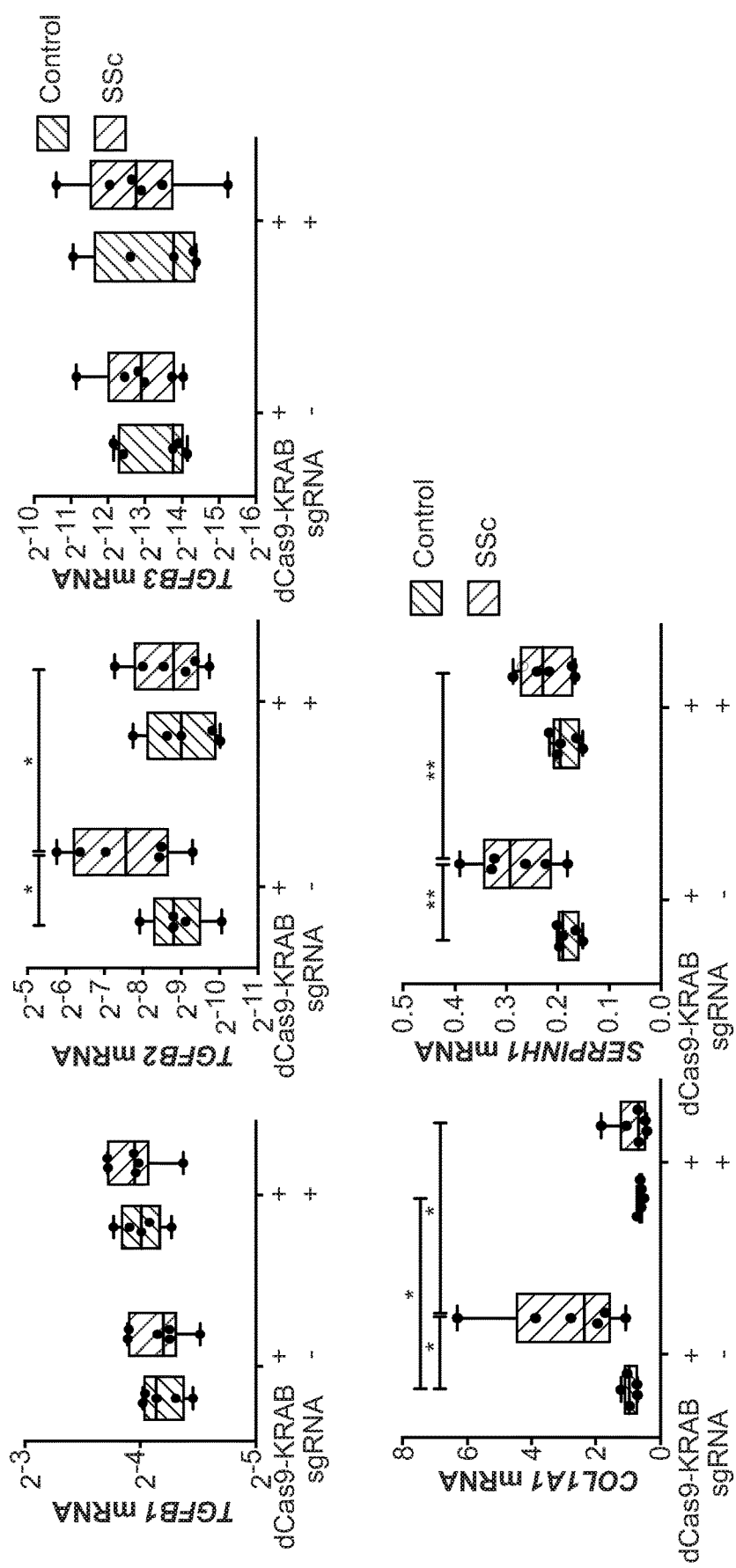

TARGETED EPIGENETIC THERAPY AGAINST DISTAL REGULATORY ELEMENT OF TGFβ2 EXPRESSION

CROSS REFERENCE TO RELATED APPLICATIONS

This Application is a national phase application filed under 35 U.S.C. § 371 of PCT International Application No. PCT/US18/022984 having an International Filing Date of 16 Mar. 2018, which claims the benefit of U.S. Provisional Patent Application No. 62/624,024 filed on Jan. 30, 2018, U.S. Provisional Patent Application 62/532,525 filed on Jul. 14, 2017 and U.S. Provisional Patent Application 62/472,955 filed on Mar. 17, 2017. The entire contents of these applications are incorporated herein by reference in their entirety.

GOVERNMENT SUPPORT

This invention was made with government support under Grant No.: R01AR068379 awarded by the National Institutes of Health. The government has certain rights in the invention.

FIELD OF THE INVENTION

Embodiments of the invention are directed to compositions that target regulatory elements of TGFβ2 expression for the treatment of Scleroderma, fibrotic disease and other TGFβ2-associated diseases and associated disorders thereof. Methods of treatment include one or more of such compositions, to patients in need thereof.

BACKGROUND

Systemic Sclerosis (Scleroderma, SSc) is a complex trait disease of unknown etiology. It is a rare connective tissue disorder characterized by chronic inflammation and severe fibrosis of the skin in addition to vasculopathy and variable fibrosis of the internal organs. Visceral complications are not uncommon in Scleroderma patients, and are associated with a 40% chance of 10-year survival (Shah A A and Wigley F M (2013). *Mayo Clin Proc.* 88: 377-393). Thus far, neither the genetic basis of Scleroderma nor the molecular mechanisms of disease progression are known (Radstake T et al. (2010). *Nature.* 42:426-432; Murdaca G (2016). *Autoimmunity Reviews.* 15:427-432). As a result, clinical treatment of Scleroderma is limited to symptomatic management of inflammation that is non-specific with varying efficacy against fibrosis, underscoring the urgent need for a better understanding of the genetic and molecular cause of Scleroderma.

SUMMARY

As described below, the present disclosure features compositions and methods for the treatment of Scleroderma, fibrotic disease and other TGFβ2-associated diseases, disorders and conditions.

In certain embodiments, a method for treating a subject having or at risk of developing a transforming growth factor β2-associated disease, disorder and/or condition comprises administering to the subject an effective amount of one or more agents that modulate transforming growth factor β2 (TGFβ2) expression by targeting an enhancer sequence distal to a TGFβ2 locus, thereby treating the subject.

In one embodiment, the TGFβ2-associated disease, disorder and/or condition is Scleroderma and/or a fibrotic disease. In another embodiment, the TGFβ2-associated disease, disorder and/or condition is grade 4 glioblastoma (GBM) or Primary Open-Angle Glaucoma (POAG).

In certain embodiments, a method of treatment optionally includes administering to a patient any one or more pharmaceutical compositions that alleviate symptoms or are therapeutically effective. For example, anti-inflammatory agents, anti-pyretic agents, antibiotics, anti-virals, chemotherapy and the like.

In certain embodiments, the TGFβ2 enhancer sequence is located distal to the TGFβ2 locus. In one embodiment, the TGFβ2 enhancer sequence is Enhancer 4514 (chr1 218632917-218634115).

In certain embodiments, one or more agents modulate activity of one or more molecules at the enhancer sequence and/or inhibit binding to the enhancer sequence and/or inactivate the enhancer functions and/or activities.

In certain embodiments, the one or more agents: increase histone deacetylase activity, inhibit histone acetyltransferase activity, inhibit BRD4 activity or combinations thereof, as compared to a normal control at the enhancer sequence.

In another embodiment, an agent that inhibits acylation of a TGFβ2 enhancer sequence or promotes deacetylation of a TGFβ2 enhancer sequence is an inhibitor of CBP/P300. Optionally, the inhibitor of CBP/P300 is bromodomain inhibitor SGC-CBP30, C646, C375 or C146. Optionally, the inhibitor of CBP/P300 is an anti-CBP/P300 inhibitory RNA or is a CRISPR/Cas agent that targets the CBP/P300 locus. In certain related embodiments, the inhibitory RNA is an antisense RNA, a siRNA or a Dicer substrate siRNA. Optionally, the CRISPR/Cas agent that targets the CBP/P300 locus comprises a loss-of-function mutation within the acetyltransferase domain. In a related embodiment, the CRISPR/Cas agent that targets the CBP/P300 locus is dCas9-EP300$^{\Delta}$.

In one embodiment, the agent that inhibits acylation of a TGFβ2 enhancer sequence or promotes deacetylation of a TGFβ2 enhancer sequence is a histone deacetylase (HDAC).

In certain embodiments, an inhibitor of BRD4 is JQ1.

In certain embodiments, an agent that modulates NF-κB activity is also administered to a patient in need of such treatment. In some embodiments, the agent inhibits NF-κB activity.

In other embodiments, a pharmaceutical composition comprising a therapeutically effective amount of at least one agent, wherein the at least one agent comprises an activator of histone deacetylase activity, an inhibitor of histone acetyltransferase activity, an inhibitor of BRD4 activity, an inhibitor of NF-κB, or any combinations thereof, as compared to a normal control.

In some embodiments the pharmaceutical composition further comprises one or more agents that modulate transforming growth factor β target gene expression. In some embodiments, the target gene comprises SMARC1, Estrogen Related Receptor 1 (ERR1), or combinations thereof.

In another preferred embodiment, a method of identifying a candidate agent for treating a transforming growth factor β2-associated disease, disorder and/or condition comprises contacting a cell comprising an enhancer sequence which modulates transforming growth factor β2 (TGFβ2) expression with a candidate agent; and, comparing expression levels of TGFβ2 with a normal control; wherein the candidate agent inhibits of TGFβ2 expression.

In certain embodiments, a method for treating a subject having transforming growth factor β2-associated disease, disorder and/or condition, comprises administering to the subject an effective amount of one or more agents that modulate transforming growth factor β2 (TGFβ2) expression by targeting an enhancer sequence distal to a TGFβ2 locus, thereby treating the subject.

In one aspect, a fibrotic synthetic repertoire (FSR) comprising one or more pro-fibrotic markers, is diagnostic of a transforming growth factor β2-associated disease, disorder and/or condition. An FSR comprises expression of one or more markers comprising COL1A1, SERPINH1 or combinations thereof, and/or TGFβ2 expression.

In another aspect, the transforming growth factor β2-associated disease, disorder and/or condition is Scleroderma and/or a fibrotic disease.

In certain embodiments, the one or more agents: modulates histone deacetylase activity, modulate histone methyltransferase activity, modulates histone acetyltransferase activity, inhibit BRD4 activity or expression thereof, inhibits NF-κB activity or expression thereof, inhibit acylation of a TGFβ2 enhancer sequence, promotes deacetylation of a TGFβ2 enhancer sequence, inhibits TGFβ2 transcription, or combinations thereof.

In certain embodiments, the one or more agents comprise: antibodies, gene-editing agents, kinase inhibitors, siRNA's, enzyme inhibitors, small molecules or combinations thereof. In certain aspects, the agent modulates histone methyltransferase activity comprises a Cas9 conjugated to a KRAB domain and specifically targeted to the TGFβ2 enhancer sequence by one or more guide RNAs.

In certain embodiments, the TGFβ2 enhancer sequence is Enhancer 4514 (chr1 218632917-218634115), variants or fragments thereof.

In another embodiment, a method of treating a subject having transforming growth factor β2-associated disease, disorder and/or condition, comprises administering to the subject an isolated nucleic acid sequence encoding a gene-editing complex comprising a Clustered Regularly Interspaced Short Palindromic Repeat (CRISPR)-associated endonuclease and at least one guide RNA (gRNA), the gRNA being complementary to a target sequence in an enhancer distal to a transforming growth factor β2 (TGFβ2), wherein the gene editing complex normalizes expression of TGFβ2, thereby treating the subject. In an embodiment, the TGFβ2 enhancer sequence is Enhancer 4514 (chr1 218632917-218634115), variants or fragments thereof.

In certain embodiments, at least one gRNA includes at least a first gRNA that is complementary to a target sequence in the enhancer; and a second gRNA that is complementary to another target sequence in the enhancer, whereby the intervening sequences between the two gRNAs are removed and/or a loss-of-function mutation is introduced into the target sequence. In certain embodiments, the one or more target sequences are associated with: histone deacetylase activity, histone methyltransferase activity, histone acetyltransferase activity, BRD4 activity or expression thereof, NF-κB activity or expression thereof, acylation of a TGFβ2 enhancer sequence, deacetylation of a TGFβ2 enhancer sequence, TGFβ2 transcription, or combinations thereof.

In certain embodiments, the CRISPR/Cas comprises catalytically deficient Cas protein (dCas), orthologs, homologs, mutants variants or fragments thereof.

In certain embodiments, an isolated nucleic acid encoding: a guide nucleic acid, wherein the guide nucleic acid comprises a targeting nucleotide sequence directed to one or more target sequences in an enhancer distal to a transforming growth factor β2 (TGFβ2); a Clustered Regularly Interspaced Short Palindromic Repeat (CRISPR)-associated endonuclease/Cas (CRISPR/Cas), comprising CRISPR/Cas tethered or conjugated to one or more modulators associated with TGFβ2 expression.

In certain embodiments, one or more modulators are fused or tethered to the CRISPR/Cas comprise modulators of: histone deacetylase activity, histone methyltransferase activity, histone acetyltransferase activity, BRD4 activity or expression thereof, NF-κB activity or expression thereof, acylation of a TGFβ2 enhancer sequence, deacetylation of a TGFβ2 enhancer sequence, TGFβ2 transcription, or combinations thereof. In certain embodiments, the CRISPR/Cas fusion protein comprises catalytically deficient Cas protein (dCas), orthologs, homologs, mutants variants or fragments thereof, fused with one or more transcriptional activators.

Other aspects are described infra.

Definitions

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense oligonucleotides, siRNA reagents, antibodies, antibody fragments bearing epitope recognition sites, such as Fab, Fab', F(ab')$_2$ fragments, Fv fragments, single chain antibodies, antibody mimetics (such as DARPins, affibody molecules, affilins, affitins, anticalins, avimers, fynomers, Kunitz domain peptides and monobodies), peptoids, aptamers; enzymes, peptides organic or inorganic molecules, natural or synthetic compounds and the like. An agent can be assayed in accordance with the methods of the invention at any stage during clinical trials, during pre-trial testing, or following FDA-approval.

By "ameliorate" is meant decrease, suppress, attenuate, diminish, arrest, or stabilize the development or progression of a disease.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., 1991 Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

As used in this specification and the appended claims, the term "or" is generally employed in its sense including "and/or" unless the content clearly dictates otherwise.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "disease" is a state of health of an animal wherein the animal cannot maintain homeostasis, and wherein if the disease is not ameliorated then the animal's health continues to deteriorate. Examples of diseases include Systemic Sclerosis (Scleroderma, SSc), other fibrotic disease and other TGFβ2-associated diseases, disorders and conditions (e.g., grade 4 glioblastoma (GBM) and Primary Open-Angle Glaucoma (POAG)).

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

The terms "pharmaceutically acceptable" (or "pharmacologically acceptable") refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "TGFβ2-associated disease, disorder and/or condition" is meant any disease, disorder and/or condition that has been identified or may be identified as associated with altered expression and/or activity of TGFβ2. Exemplary TGFβ2-associated diseases, disorders and/or conditions of the instant disclosure include those associated with upregulation of TGFβ2 (optionally induced by distal enhancer sequence(s) of TGFβ2), such as Scleroderma, other fibrotic disease, grade 4 glioblastoma (GBM) and/or Primary Open-Angle Glaucoma (POAG).

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human. The term "gene" is also intended to include variants.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

BRIEF DESCRIPTION OF THE DRAWINGS

FIG. 1D: Effects of TGFβ2 ligand stimulation on collagen expression was assessed in SSc fibroblasts. FIG. 1E: Effects of autocrine TGFβ2 signaling on mRNA expression of collagen was assessed through treatment of control and SSc fibroblasts with anti-TGFβ2 neutralizing antibody, followed by RT-qPCR. FIG. 1F: Effects of autocrine TGFβ2 stimulation on mRNA expression of TGFβ2 was assessed through treatment of control and SSc fibroblasts with combinations of anti-TGFBβ2 neutralizing antibody and exogenous TGFβ2 ligand (long/mL).

FIG. 3A shows H3K27ac ChIPseq tracks from ENCODE at Enhancer 4514. FIG. 3E: Control or SSc fibroblasts were transfected with dCas9-KRAB with sgRNA targeted to enhancer 4514. mRNA transcript levels were measured 72 hours post-transfection by RT-qPCR.

FIGS. 4A to 4N show that NF-κB and BRD4 maintain epigenetic activity of the TGFB2 enhancer in SSc. FIGS. 4A and 4B, show that treatment with the EP300 inhibitor (SGC-CBP30, 72 hours) suppressed TGFB2 mRNA expression and P300 occupancy of the TGFB2 enhancer in SSc fibroblasts, both of which rebounded to steady-state levels in SSc fibroblasts upon drug removal. FIG. 4 CCHIP-qPCR revealed elevated occupancy of BRD4 and acetylated p65 (activated NF-kB) at the TGFB2 enhancer in cultured SSc fibroblasts. FIG. 4N: JQ1-treated SSc fibroblasts cluster with control fibroblasts in principle component analysis (PC1 accounts for 67% of total variance). *P<0.05; P<0.01; *P<0.001. Blue and red bars represent control and SSc fibroblasts, respectively. $N_{control}$=5 and $N_{SSc}$=6. Lower and upper margins of each bar indicate $25^{th}$ and $75^{th}$ percentiles, respectively; the internal line indicates the mean and whiskers indicate the range. Black points represent individual samples. All mRNA levels were normalized to GAPDH mRNA levels, respectively. All experiments other than RNA-seq and ATAC-qPCR were repeated at least twice with similar results.

DETAILED DESCRIPTION

Figures 1A, 1B, 1C:
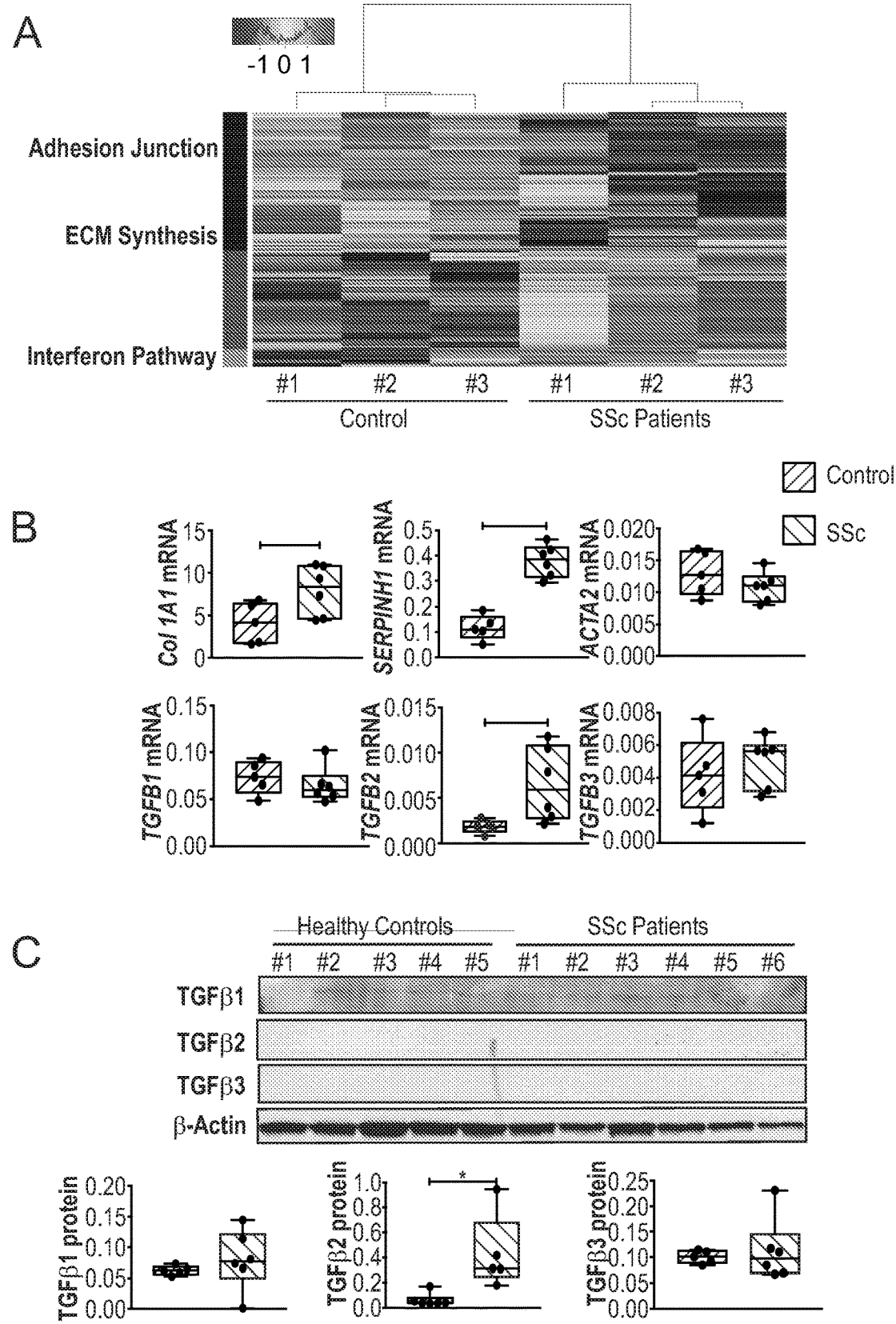
FIG. 1A is a heatmap. Primary control and SSc fibroblasts were cultured ex vivo under serum deprived conditions (DMEM+1% FCS). Unsupervised hierarchical clustering was performed on genes with significant mRNA expression differences (FDR<0.05) assessed by RNA-seq on primary control and SSc fibroblasts. Top ranked GO term result for each gene cluster is indicated on the left of the heatmap.
FIG. 1B are plots showing mRNA transcript levels measured by RT-qPCR.
FIG. 1C: Transcript differences were correlated with protein expression by western blot under same culture conditions.

The instant disclosure is based, at least in part, upon the discovery that upregulation of expression of TGFβ2, specifically provoked by increased acylation of distal enhancer sequence(s) of TGFβ2, is associated with the presence and/or progression of Scleroderma.

Such a discovery implicates administration of agents that inhibit acylation of a TGFβ2 enhancer sequence or promote deacetylation of a TGFβ2 enhancer sequence as a therapeutic, while also identifying diagnostic assessment of the acylation state of TGFβ2 enhancer sequence(s) as a biomarker relevant to TGFβ2-associated diseases, disorders and/or conditions (e.g., Scleroderma, other fibrotic disease, grade 4 glioblastoma (GBM) and/or Primary Open-Angle Glaucoma (POAG)).

Without wishing to be bound by theory, the data obtained herein show that increased occupancy of P300 and BRD4 at Enhancer 4514 (Chr1: 218632917-218634115, hg19) is driving TGFβ2 expression, which in turn drives the expression of pro-fibrotic genes in SSc fibroblasts. Moreover modification of this open chromatin epigenetic mark, through pharmacological inhibition of histone acetyltransferases, is sufficient to transiently normalize TGFβ2 expression. JQ1 was also discovered as a novel therapeutic drug for the treatment of Systemic Sclerosis. Specifically, it was found that JQ1 permanently normalizes TGFβ2 mRNA expression in SSc fibroblasts with a single 48 hr regiment through specific inhibition of BRD4 occupying enhancer 4514. The therapeutic efficacy of inhibiting NF-kB in Systemic Sclerosis was also demonstrated.

Accordingly, certain embodiments are directed to agents that increase histone deacetylase activity, inhibit histone acetyltransferase activity or inhibit BRD4 activity at Enhancer 4514 as therapeutic agents for scleroderma and potentially other fibrotic diseases.

TGFβ2 and Scleroderma

Fibrotic skin of Scleroderma patients has been identified invariably as associated with heightened levels of TGFβ signaling (Shah and Wigley. *Mayo Clin Proc.* 88: 377-393). Since high levels of TGFβ signaling is sufficient to drive fibrosis (Sonnylal et al. *Arthritis and Rheumatism* 56:334-344), it was hypothesized that dermal fibroblasts of Scleroderma patients might be expressing high levels of TGFβ ligand, creating a positive-feedback mechanism that perpetually promotes fibrosis. While heightened deposition of TGFβ1 and TGFβ2 ligand in the dermal layer of Scleroderma skin has been observed by immunohistochemistry (Sfikakis et al. *Clinical Immunology and Immunopathology* 69:199-204), the role of TGFβ2 in Scleroderma pathogenesis has remained unknown, and has specifically to date remained unclear how TGFβ2 expression is regulated in normal fibroblasts or Scleroderma fibroblasts.

The instant data provide what is believed to be the first functional evidence that Scleroderma fibroblasts express significantly higher levels of TGFβ2 ligand than control cells ex vivo. Also, inhibition of TGFβ2 ligand stimulation normalized the heightened levels of Type 1 Collagen found in Scleroderma fibroblasts. These results also demonstrated that heightened TGFβ2 ligand expression in Scleroderma was due to heightened activation of a novel enhancer, which has been identified herein through the unique use of combined ATAC-sequencing profile of primary fibroblasts and published ENCODE databases. These methods have allowed for an unprecedented ability to determine the activation status of a novel TGFβ2 enhancer, which will likely prove clinically useful as a biomarker for Scleroderma disease progression. It has also been established herein that modification of epigenetic marks at the TGFβ2 enhancer using CRISPR can activate TGFβ2 expression. Conversely, treatment with small-molecule inhibitors of histone acetyltransferases (SGC-CBP300) can specifically decrease the expression of TGFβ2, but not TGFβ1 or TGFβ3. In sum, these results have identified a novel biomarker and treatment strategy/therapeutic target for Scleroderma and other diseases associated with heightened TGFβ2 expression.

High TGFβ2 in Other Diseases

Various diseases other than Scleroderma have also been associated with significantly high levels of TGFβ2. Thus, patients with conditions other than Scleroderma are likely to benefit from using the activation status of TGFβ2 enhancer to monitor disease progression and/or from using epigenetic modifiers of the TGFβ2 enhancer as treatment. Considered one of the most aggressive cancers, a subset of grade 4 glioblastoma (GBM) is driven by heightened levels of TGFβ2 (Rodon et al. *Cancer Discovery* 4:1230-41), and high TGFβ2 activity correlates with worse prognosis among GBM subtypes. Currently, a few patients with GBM have benefited from TGFβ inhibitors, underscoring the need for better methods of inhibiting TGFβ2 activity and expression. Additionally, there are currently no methods to accurately stratify which patients exhibit high TGFβ2 activity in their cancer cells, highlighting the need for an accurate biomarker of high TGFβ2 activity. Assessing the activity of the TGFβ2 enhancer will likely aid stratifying GBM subtypes that exhibit high TGFβ2 activity. Furthermore, since TGFβ2 has been shown to establish an autocrine loop mechanism in GBM (Rodon et al. *Cancer Discovery* 4:1230-41), epigenetic targeting of the TGFβ2 enhancer will likely prove efficacious in treating Type 4 GBM.

High levels of TGFβ2 have also been shown to be pathogenic in the development of Primary Open-Angle Glaucoma (POAG; Fuchshofer et al. *Cell Tissue Research* 347:279-90), a major cause of blindness worldwide. Heightened TGFβ2 expression promotes elevated extracellular matrix synthesis in the trabecular meshwork and around the optic nerve, thereby elevating pathologically high intraocular pressure. Current treatment options for POAG are limited to adrenergic antagonists with various efficacy or invasive surgical procedures, highlighting the need for small-molecule inhibitors that may specifically regulate TGFβ2 through epigenetic modifications. These patients will likely also benefit from using the activation status of TGFβ2 enhancer to predict the onset of POAG and/or monitor disease progression.

Diagnostic and Therapeutic Applications

Detecting activation status of TGFβ2 enhancer: To determine the activation status of the enhancer for TGFβ2 expression, chromatin immunoprecipitation was performed, followed by quantitative PCR (CHIP-qPCR), using primers that were uniquely designed based on ATAC-seq data for primary fibroblasts and published ENCODE data. The current method of detecting the activation status of TGFβ2 enhancer was implemented on primary human fibroblast cell lines established from dermal biopsies of normal controls or Scleroderma patients. However, the current method is applicable to adherent or non-adherent cells from tissue or blood of subjects (e.g., human patients).

A detailed description of the reagents and methods used in the detection and identification of the TGFβ2 enhancer activation is described in the "Examples" section which follows. By way of a brief summary, using RNAseq, it was found that primary dermal fibroblasts (PDFs) from SSc patients maintain a strong fibrotic synthetic repertoire (FSR) after many passages in culture (e.g. COL1A1, SERPINH1). This correlated with specific upregulation of TGFβ2 (but not β1 or β3) mRNA and protein expression that was prone to further amplification by TGFβ treatment. Use of a TGFβ receptor kinase inhibitor or a specific TGFβ2-neutralizing antibody fully silenced the FSR in SSc cells. Together, these data provided evidence for a mechanism to "lock in" the FSR in SSc, with particular relevance for TGFβ2. Epigenetic regulation of gene expression was posited as an integrator of both genetic and environmental triggers. ATACseq revealed an open chromatin conformation for a sequence-constrained region just distal to the TGFB2 gene in SSc PDFs, with direct correlation between accessibility and TGFβ2 mRNA levels. This element was enriched for acetylated H3K27 and occupancy by the histone acetyltransferase (HAT) EP300. CRISPR-based targeting of HAT activity to this element was sufficient to induce or accentuate TGFβ2 expression in control or SSc PDFs, respectively, validating functional enhancer status. Strikingly, CRISPR-based targeting of histone methyltransferase activity normalized TGFβ2 and pro-fibrotic gene expression in SSc PDFs. Treatment of SSc cells with a HAT inhibitor (HATi) was sufficient to normalize TGFβ2 expression and silence the FSR, but full rebound occurred within 72 hrs after drug removal. This indicated that epigenetic modifications that activate the TGFβ2 enhancer contribute to the maintenance of pro-fibrotic gene expression in SSc. These findings were evidence of super-enhancer priming that can be initiated by inflammatory effectors (e.g. NF-κB) and enforced by BRD4 recruitment. In support of this hypothesis, high NF-kB and BRD4 occupancy was found at the implicated TGFβ2 enhancer in SSc PDFs. Unlike the prior rebound experience with HATi, treatment with the BRD4 inhibitor JQ1 led to normalization of TGFβ2 expression and the FSR that was maintained even after drug removal. JQ1 treatment mitigated transcriptomic differences between control and SSc PDFs, and this occurred with complete normalization of BRD4 occupancy and chromatin accessibility of the TGFβ2 enhancer in SSc PDFs. Taken together, this data provides an explanation for the pathogenesis of SSc and identifies both therapeutic targets and biomarkers for use in clinical trials.

Histone acetyltransferase inhibition (HATi) decreased TGFβ2: Based on the discovery that a novel enhancer activated TGFβ2 expression in Scleroderma, it was hypothesized that the inhibition of epigenetic marks that activate enhancers might decrease TGFβ2 expression in Scleroderma cells. Enhancers are activated upon the acquisition of a histone modification known as Histone 3 Lysine 27 Acetylation (H3K27ac). CBP/P300 is the major enzyme that creates H3K27ac modification to enhancer sequences. Thus, purchased generic, commercially available drugs against CBP/P300 were purchased for further study (list provided below). SGC-CBP30 treatment was found to specifically decrease TGFβ2 expression in Scleroderma cells to levels comparable to that of control, with minimal cell toxicity. These results have incentivized further testing using animal models of Scleroderma, and highlight a novel therapeutic avenue for Scleroderma and other diseases associated with TGFβ2, such as Grade 4 Glioblastoma and Primary Open Angle Glaucoma.

P300 Inhibitor List:

SGC-CPB30 (Sigma, #SML1133)

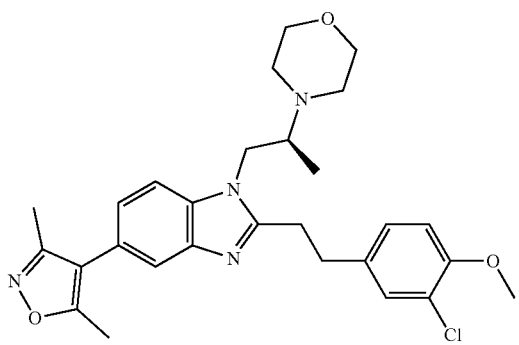

C646 (Selleckchem, #S7152)

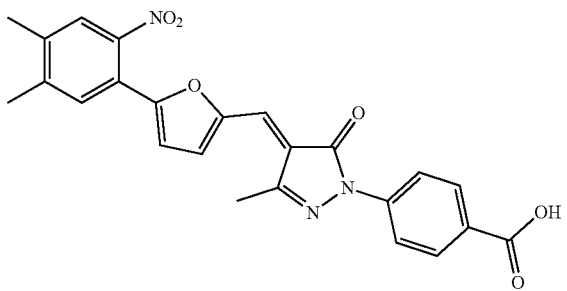

C375 (Chembridge #6643375)

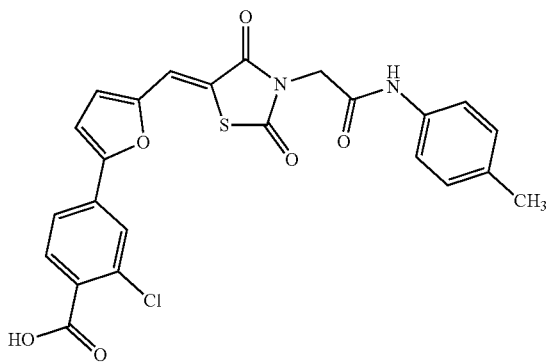

C146 (Chembridge #5202146)

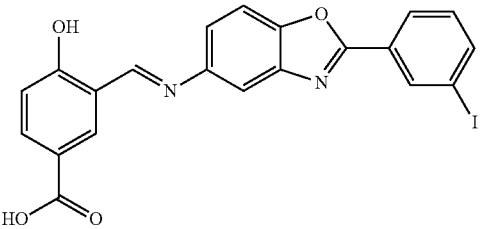

P300 Sequence: Certain agents of the instant disclosure target the P300 transcript (P300 Transcript (NM_001429.3)) and/or polypeptide (P300 Polypeptide (NP_001420.2)).

Systemic Sclerosis (SSc)

Systemic Sclerosis (Scleroderma, SSc) is a complex trait disease of unknown etiology. It is a rare connective tissue disorder characterized by chronic inflammation and severe fibrosis of the skin in addition to vasculopathy and variable fibrosis of the internal organs. Visceral complications are not uncommon in Scleroderma patients, and are associated with a 40% chance of 10-year survival (Shah and Wigley. *Mayo Clin Proc.* 88: 377-393). To date, neither the genetic basis of Scleroderma nor the molecular mechanisms of disease progression have been established (Radstake et al. *Nature* 42:426-432; Murdaca G. *Autoimmunity Reviews* 15:427-432). As a result, clinical treatment of Scleroderma is currently limited to symptomatic management of inflammation that is non-specific with varying efficacy against fibrosis, underscoring the urgent need for a better understanding of the genetic and molecular cause of Scleroderma.

Lesional skin of Scleroderma patients has consistently been associated with heightened levels of transforming growth factor β (TGFβ) signaling in dermal fibroblasts. Elevated TGFβ signaling is sufficient to drive dermal fibrosis, as evidenced in various animal models of fibrosis (Sonnylal et al. *Arthritis and Rheumatism* 56:334-344). In line with prior literature, it was previously observed that primary SSc fibroblasts maintained higher expression of TGFβ target genes, such as type 1 collagen, when cultured ex vivo under serum-deprived conditions (Gerber et al. *Nature* 503:126-130). These results suggested that SSc fibroblasts maintained a pro-fibrotic synthetic repertoire ex vivo. However, large-scale genomic and exomic screens of SSc patients have not identified genomic variants with clear biological function (Murdaca G. *Autoimmunity Reviews* 15:427-432). Therefore, it has thus far remained unclear how SSc fibroblasts can stably maintain pro-fibrotic transcriptomic differences ex vivo. The instant disclosure begins to address this issue—identifying the activity of Enhancer 4514 of TGFβ2 advances understanding of the etiology of Scleroderma, and helps to identify therapeutic targets for Scleroderma and many fibrotic diseases driven by TGFβ (particularly TGFβ2).

The observation that the Scleroderma concordance rate of monozygotic twins is merely 4%, comparable to that of dizygotic twins (Feghali-Bostwick et al. *Arthritis and Rheumatism* 48:1956-1963), indicated that genetic variation cannot solely account for Scleroderma etiology.

Other Fibrotic Diseases and Disorders

Fibrosis is the formation of excess fibrous connective tissue in an organ or tissue in a reparative or reactive process (Birbrair et al. *Stem Cell Research & Therapy.* 5 (6): 122). This can be a reactive, benign, or pathological state. In response to injury, this is called scarring, and if fibrosis arises from a single cell line, this is called a fibroma. Physiologically, fibrosis acts to deposit connective tissue, which can obliterate the architecture and function of the underlying organ or tissue. Fibrosis can be used to describe the pathological state of excess deposition of fibrous tissue, as well as the process of connective tissue deposition in healing. Defined by the pathological accumulation of extracellular matrix (ECM) proteins, fibrosis results in scarring and thickening of the affected tissue, it is in essence an exaggerated wound healing response which interferes with normal organ function. Examples of non-Scleroderma fibrotic diseases and disorders include:

Lungs: Pulmonary fibrosis, Cystic fibrosis, Idiopathic pulmonary fibrosis (idiopathic meaning the cause is unknown), Radiation-induced lung injury following treatment for cancer.

Liver: Cirrhosis.

Heart: Atrial Fibrosis, Endomyocardial fibrosis, Old myocardial infarction.

Brain: glial scar.

Other: Arterial stiffness, Arthrofibrosis (knee, shoulder, other joints), Crohn's Disease (intestine), Dupuytren's contracture (hands, fingers), Keloid (skin), Mediastinal fibrosis (soft tissue of the mediastinum), Myelofibrosis (bone marrow), Peyronie's disease (penis), Nephrogenic systemic fibrosis (skin), Progressive massive fibrosis (lungs); a complication of coal workers' pneumoconiosis, Retroperitoneal fibrosis (soft tissue of the retroperitoneum), some forms of adhesive capsulitis (shoulder)

Other TGFβ2-Associated Diseases and Disorders

Grade 4 Glioblastoma (GBM): Glioblastoma, also known as glioblastoma multiforme (GBM), is the most aggressive cancer that begins within the brain (Bleeker et al. *Journal of Neuro-Oncology.* 108 (1): 11-27). Signs and symptoms of glioblastoma are initially non-specific. They may include headaches, personality changes, nausea, and symptoms similar to those of a stroke (Young et al. *Annals of Translational Medicine* 3 (9): 121). Worsening of symptoms is often rapid. This can progress to unconsciousness (*World Cancer Report* 2014. World Health Organization. 2014. pp. Chapter 5.16).

The cause of most cases is unclear (Id.). Uncommon risk factors include genetic disorders such as neurofibromatosis and Li Fraumeni syndrome and previous radiation therapy (Id.; Gallego, O. *Current oncology* (Toronto, Ont.). 22 (4): e273-81). Glioblastomas represent 15% of brain tumors (Young et al. *Annals of Translational Medicine* 3 (9): 121). They can either start from normal brain cells or develop from an already existing low-grade astrocytoma (*World Cancer Report* 2014. World Health Organization. 2014. pp. Chapter 3.8). The diagnosis is typically made by a combination of CT scan, MRI scan, and tissue biopsy (Young et al. *Annals of Translational Medicine* 3 (9): 121).

There is no clear way to prevent the disease. Typically treatment involves surgery after which chemotherapy and radiation therapy are used (Gallego, O. *Current oncology* (Toronto, Ont.). 22 (4): e273-81). The medication temozolomide is frequently used as part of chemotherapy (Id.; Khosla, D. *Annals of translational medicine.* 4 (3): 54; Hart, M G; Garside et al. *The Cochrane database of systematic reviews.* 4: CD007415). High dose steroids may be used to help reduce swelling and decrease symptoms (Young et al. *Annals of Translational Medicine* 3 (9): 121). It is unclear whether trying to remove all or simply most of the cancer is better (Van Meir et al. *CA: A Cancer Journal for Clinicians.* 60 (3): 166-93).

Despite maximum treatment, the cancer usually recurs (Gallego, O. *Current oncology* (Toronto, Ont.). 22 (4): e273-81). The most common length of survival following diagnosis is 12 to 15 months with less than 3% to 5% of people surviving longer than five years (Id.; *World Cancer Report* 2014. World Health Organization. 2014. pp. Chapter 5.16). Without treatment survival is typically 3 months (Schapira, Anthony H. V. Neurology and clinical neuroscience. Philadelphia: Mosby Elsevier. p. 1336). It is the most common cancer that begins within the brain and the second most common brain tumor after meningioma (Bleeker et al. *Journal of Neuro-Oncology.* 108 (1): 11-27; McNeill, Katharine A. *Neurologic Clinics.* 34 (4): 981-998). About 3 per 100,000 people develop the disease a year (Gallego, O. *Current oncology* (Toronto, Ont.). 22 (4): e273-81). It most often begins around 64 years of age and occurs more commonly in males than females (Id.; *World Cancer Report* 2014. World Health Organization. 2014. pp. Chapter 5.16). Immunotherapy is being studied in glioblastoma with promising results ("With Immunotherapy, Glimmers of Progress against Glioblastoma". *National Cancer Institute.* 9 Dec. 2015).

Primary Open Angle Glaucoma: Glaucoma is a group of eye diseases which result in damage to the optic nerve and vision loss ("Facts About Glaucoma". *National Eye Institute.* Retrieved 29 Mar. 2016). The most common type is open-angle glaucoma with less common types including closed-angle glaucoma and normal-tension glaucoma. Open-angle glaucoma develops slowly over time and there is no pain. Side vision may begin to decrease followed by central vision resulting in blindness if not treated (Id.). Closed-angle glaucoma can present gradually or suddenly (Mantravadi and Vadhar. *Primary Care.* Saunders (Elsevier). 42 (3): 437-49). The sudden presentation may involve severe eye pain, blurred vision, mid-dilated pupil, redness of the eye, and nausea ("Facts About Glaucoma". National Eye Institute. Retrieved 29 Mar. 2016; Mantravadi and Vadhar. *Primary Care.* Saunders (Elsevier). 42 (3): 437-49). Vision loss from glaucoma, once it has occurred, is permanent "Facts About Glaucoma". National Eye Institute. Retrieved 29 Mar. 2016).

Risk factors for glaucoma include increased pressure in the eye, a family history of the condition, migraines, high blood pressure, and obesity (Id.). For eye pressures a value of greater than 21 mmHg or 2.8 kPa is often used with higher pressures leading to a greater risk (Mantravadi and Vadhar. *Primary Care.* Saunders (Elsevier). 42 (3): 437-49; Rhee, Douglas J. Glaucoma (2 ed.). Philadelphia: Wolters Kluwer Health/Lippincott Williams & Wilkins. p. 180). However, some may have high eye pressure for years and never develop damage (Mantravadi and Vadhar. *Primary Care.* Saunders (Elsevier). 42 (3): 437-49). Conversely, optic nerve damage may occur with normal pressure, known as normal-tension glaucoma (Mi et al. *Clinical Interventions in Aging.* 9: 1563-71). The mechanism of open-angle glaucoma is believed to be slow exit of aqueous humor through the trabecular meshwork while in closed-angle glaucoma the iris blocks the trabecular meshwork (Mantravadi and Vadhar. *Primary Care.* Saunders (Elsevier). 42 (3): 437-49). Diagnosis is by a dilated eye examination ("Facts About Glaucoma". National Eye Institute. Retrieved 29 Mar. 2016). Often the optic nerve shows an abnormal amount of cupping (Mantravadi and Vadhar. *Primary Care.* Saunders (Elsevier). 42 (3): 437-49).

If treated early it is possible to slow or stop the progression of disease with medication, laser treatment, or surgery ("Facts About Glaucoma". National Eye Institute. Retrieved 29 Mar. 2016). The goal of these treatments is to decrease eye pressure. A number of different classes of glaucoma medication are available. Laser treatments may be effective in both open-angle and closed-angle glaucoma. A number of types of glaucoma surgeries may be used in people who do not respond sufficiently to other measures (Mantravadi and Vadhar. *Primary Care*. Saunders (Elsevier). 42 (3): 437-49). Treatment of closed-angle glaucoma is a medical emergency ("Facts About Glaucoma". National Eye Institute. Retrieved 29 Mar. 2016).

About 11 to 67 million people have glaucoma globally (Mantravadi and Vadhar. *Primary Care*. Saunders (Elsevier). 42 (3): 437-49; Global Burden of Disease Study 2013, Collaborators (22 Aug. 2015). *Lancet* (London, England). 386 (9995): 743-800). The disease affects about 2 million people in the United States (Mantravadi and Vadhar. *Primary Care*. Saunders (Elsevier). 42 (3): 437-49). It occurs more commonly among older people ("Facts About Glaucoma". National Eye Institute. Retrieved 29 Mar. 2016). Closed-angle glaucoma is more common in women (Mantravadi and Vadhar. *Primary Care*. Saunders (Elsevier). 42 (3): 437-49). Glaucoma has been called the "silent thief of sight" because the loss of vision usually occurs slowly over a long period of time (Glaucoma: The 'silent thief' begins to tell its secrets" (Press release). National Eye Institute. 21 Jan. 2014). Worldwide, glaucoma is the second-leading cause of blindness after cataracts (Mantravadi and Vadhar. *Primary Care*. Saunders (Elsevier). 42 (3): 437-49; Resnikoff et al. *Bulletin of the World Health Organization*. 82 (11): 844-51). The word "glaucoma" is from ancient Greek glaukos which means blue, green, or gray (Leffler et al. *Ophthalmology and Eye Diseases*. Libertas Academica. 7: 21-33). In English, the word was used as early as 1587 but did not become commonly used until after 1850, when the development of the ophthalmoscope allowed people to see the optic nerve damage (Leffler et al. *JAMA Ophthalmology*. 131 (12): 1625-31).

Agents of the Disclosure

The disclosure provides agents to modulate the acylation/deacetylation state of an enhancer element of TGFβ2. In one embodiment, the agent is an inhibitor or antagonist of an acylase (e.g., P300) and/or is an activator of a deacetylase that is active at distal enhancer sequences of TGFβ2. In a particular embodiment, the agent is bromodomain inhibitor SGC-CBP30, C646, C375 and/or C146.

Agents useful in the methods of the disclosure can be small molecules, but can also be enzymes and/or nucleic acid molecules, e.g., antisense, ribozyme, or RNA interference technology, e.g., siRNA molecules corresponding to a portion of the nucleotide sequence encoding CBP/P300.

Antisense polynucleotides may act by directly blocking translation by hybridizing to mRNA transcripts or degrading such transcripts of a gene. The antisense molecule may be recombinantly made using at least one functional portion of a gene in the antisense orientation as a region downstream of a promoter in an expression vector. Chemically modified bases or linkages may be used to stabilize the antisense polynucleotide by reducing degradation or increasing half-life in the body (e.g., methyl phosphonates, phosphorothioate, peptide nucleic acids). The sequence of the antisense molecule may be complementary to the translation initiation site (e.g., between −10 and +10 of the target's nucleotide sequence).

siRNA refers to double-stranded RNA of at least 20-25 basepairs which mediates RNA interference (RNAi). Duplex siRNA corresponding to a target RNA may be formed by separate transcription of the strands, coupled transcription from a pair of promoters with opposing polarities, or annealing of a single RNA strand having an at least partially self-complementary sequence. Alternatively, duplexed oligoribonucleotides of at least about 21 to about 23 basepairs may be chemically synthesized (e.g., a duplex of 21 ribonucleotides with 3' overhangs of two ribonucleotides) with some substitutions by modified bases being tolerated. Mismatches in the center of the siRNA sequence, however, abolishes interference. The region targeted by RNA interference should be transcribed, preferably as a coding region of the gene. Interference appears to be dependent on cellular factors (e.g., ribonuclease III) that cleave target RNA at sites 21 to 23 bases apart; the position of the cleavage site appears to be defined by the 5' end of the guide siRNA rather than its 3' end. Priming by a small amount of siRNA may trigger interference after amplification by an RNA-dependent RNA polymerase.

Nucleases: Any suitable nuclease system can be used including, for example, Argonaute family of endonucleases, clustered regularly interspaced short palindromic repeat (CRISPR) nucleases, zinc-finger nucleases (ZFNs), transcription activator-like effector nucleases (TALENs), meganucleases, other endo- or exo-nucleases, or combinations thereof. See Schiffer, 2012, *J Virol* 88(17):8920-8936, incorporated by reference. In preferred embodiments, the system is an Argonaute nuclease system.

CRISPR-Cas: In certain aspects, inhibition of acylation of TGFβ2 enhancer element(s) can be achieved by administration of inhibitory nucleic acids (e.g., dsRNAs, siRNAs, antisense oligonucleotides, etc.) directed to inhibit CBP/P300. It is also contemplated that CRISPR-Cas (e.g., CRISPR-Cas9) methods can be used to excise and replace CBP/P300 alleles. Such methods can be performed upon the cells of a subject in vivo or ex vivo. Use of any combination of the above and/or other known inhibitor of acylation of TGFβ2 enhancer element(s) is also contemplated.

The CRISPR-Cas system is known in the art. Non-limiting aspects of this system are described in U.S. Pat. No. 8,697,359, issued Apr. 15, 2014, the entire content of which is incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas 10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments, the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

Argonautes: Argonautes are a family of endonucleases that use 5' phosphorylated short single-stranded nucleic acids as guides to cleave targets (Swarts, D. C. et al. The evolutionary journey of Argonaute proteins. *Nat. Struct. Mol. Biol.* 21, 743-753 (2014)). Similar to Cas9, Argonautes have key roles in gene expression repression and defense against foreign nucleic acids (Swarts, D. C. et al. *Nat. Struct. Mol. Biol.* 21, 743-753 (2014); Makarova, K. S., et al. *Biol. Direct* 4, 29 (2009). Molloy, S. *Nat. Rev. Microbiol.* 11, 743 (2013); Vogel, J. *Science* 344, 972-973 (2014). Swarts, D. C. et al. *Nature* 507, 258-261 (2014); Olovnikov, I., et al. *Mol. Cell* 51, 594-605 (2013)). However, Argonautes differ from Cas9 in many ways (Swarts, D. C. et al. *Nat. Struct. Mol. Biol.* 21, 743-753 (2014)). Cas9 only exist in prokaryotes, whereas Argonautes are preserved through evolution and exist in virtually all organisms; although most Argonautes associate with single-stranded (ss)RNAs and have a central role in RNA silencing, some Argonautes bind ssDNAs and cleave target DNAs (Swarts, D. C. et al. *Nature* 507, 258-261 (2014); Swarts, D. C. et al. *Nucleic Acids Res.* 43, 5120-5129 (2015)). guide RNAs must have a 3' RNA-RNA hybridization structure for correct Cas9 binding, whereas no specific consensus secondary structure of guides is required for Argonaute binding; whereas Cas9 can only cleave a target upstream of a PAM, there is no specific sequence on targets required for Argonaute. Once Argonaute and guides bind, they affect the physicochemical characteristics of each other and work as a whole with kinetic properties more typical of nucleic-acid-binding proteins (Salomon, W. E., et al. *Cell* 162, 84-95 (2015)).

Argonaute proteins typically have a molecular weight of ~100 kDa and are characterized by a Piwi-Argonaute-Zwille (PAZ) domain and a PIWI domain. Crystallographic studies of archaeal and bacterial Argonaute proteins revealed that the PAZ domain, which is also common to Dicer enzymes, forms a specific binding pocket for the 3'-protruding end of the small RNA with which it associates (Jinek and Doudna, (2009) *Nature* 457, 405-412)). The structure of the PIWI domain resembles that of bacterial RNAse H, which has been shown to cleave the RNA strand of an RNA-DNA hybrid (Jinek and Doudna, (2009) *Nature* 457, 405-412)). More recently, it was discovered that the catalytic activity of miRNA effector complexes, also referred to as Slicer activity, resides in the Argonaute protein itself.

Members of the human Ago subfamily, which consists of AGO1, AGO2, AGO3 and AGO4, are ubiquitously expressed and associate with miRNAs and siRNAs. Ago proteins are conserved throughout species, and many organisms express multiple family members, ranging from one in *Schizosaccharomyces pombe*, five in *Drosophila*, eight in humans, ten in *Arabidopsis* to twenty-seven in *C. elegans* (Tolia and Joshua-Tor, (2007) *Nat. Chem. Biol.* 3, 36-43). Argonaute proteins are also present in some species of budding yeast, including *Saccharomyces castellii*. It was found that *S. castellii* expresses siRNAs that are produced by a Dicer protein that differs from the canonical Dicer proteins found in animals, plants and other fungi (Drinnenberg et al., (2009) *Science* 326, 544-550).

More recently, structural studies have been extended to *Thermus thermophilus* Argonaute in complex with a guide strand only or a guide DNA strand and a target RNA duplex. This analysis revealed that the structure of the complex is divided into two lobes. One lobe contains the PAZ domain connected to the N-terminal domain through a linker region, L1. The second lobe consists of the middle (MID) domain (located between the PAZ and the PIWI domains) and the PIWI domain. The 5' phosphate of the small RNA, to which Argonaute binds, is positioned in a specific binding pocket in the MID domain (Jinek and Doudna, (2009) *Nature* 457, 405-412). The contacts between the Argonaute protein and the guide DNA or RNA molecule are dominated by interactions with the sugar-phosphate backbone of the small RNA or DNA; thus, the bases of the RNA or DNA guide strand are free for base pairing with the complementary target RNA. The structure indicates that the target mRNA base pairs with the guide DNA strand, but does not touch the protein (Wang et al., (2008a) *Nature* 456, 921-926; Wang, Y. et al., (2009) *Nat. Struct. Mol. Biol.* 16, 1259-1266; Wang et al., (2008b) *Nature* 456, 209-213).

The useful features of Argonaute endonucleases, e.g. *Natronobacterium gregoryi* Argonaute (NgAgo) for genome editing include the following: (i) NgAgo has a low tolerance to guide-target mismatch. (ii) 5' phosphorylated short ssDNAs are rare in mammalian cells, which minimizes the possibility of cellular oligonucleotides misguiding NgAgo. (iii) NgAgo follows a 'one-guide-faithful' rule, that is, a guide can only be loaded when NgAgo protein is in the process of expression, and, once loaded, NgAgo cannot swap its gDNA with other free ssDNA at 37° C.

Accordingly, in certain embodiments, Argonaute endonucleases comprise those which associate with single stranded RNA (ssRNA) or single stranded DNA (ssDNA). In certain embodiments, the Argonaute is derived from *Natronobacterium gregoryi*. In other embodiments. the *Natronobacterium gregoryi* Argonaute (NgAgo) is a wild type NgAgo, a modified NgAgo, or a fragment of a wild type or modified NgAgo. The NgAgo can be modified to increase nucleic acid binding affinity and/or specificity, alter an enzymatic activity, and/or change another property of the protein. For example, nuclease (e.g., DNase) domains of the NgAgo can be modified, deleted, or inactivated.

The wild type NgAgo sequence can be modified. The NgAgo nucleotide sequence can be modified to encode biologically active variants of NgAgo, and these variants can have or can include, for example, an amino acid sequence that differs from a wild type NgAgo by virtue of containing one or more mutations (e.g., an addition, deletion, or substitution mutation or a combination of such mutations). One or more of the substitution mutations can be a substitution (e.g., a conservative amino acid substitution). For example, a biologically active variant of an NgAgo polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type NgAgo polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the NgAgo amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those which have not been found in nature, but that conform to the basic formula of an amino acid and can be incorporated into a peptide. These include D-alloisoleucine(2R,3S)-2-amino-3-methylpentanoic acid and Lcyclopentyl glycine (S)-2-amino-2-cyclopentyl acetic acid. For other examples, one can consult textbooks or the worldwide web (a site currently maintained by the California Institute of Technology displays structures of non-natural amino acids that have been successfully incorporated into functional proteins).

Candidate Therapeutic Agents

Candidate therapeutic agents can be screened using any number and types of assays. For example, high throughput functional genomics assays can be used to identify modulators of: TGFβ2 expression; acylation/deacetylation state of an enhancer element of TGFβ2; expression and/or function of distal enhancers; BRD4 activity; NF-κB activity or any combination thereof.

Any type of cell can be used, including ones which have been transformed with one or more vectors encoding the distal enhancer sequences, fragments or variants thereof, and TGFβ2 nucleic acid sequences. Typically, in such assays the cells are contacted with a candidate therapeutic agent, such as for example, cDNA, a random peptide library (encoded by nucleic acids), antisense reagents, antibodies etc. In cases where the agents comprise a cDNA library, the cDNA library can comprise sense, antisense, full length, and truncated cDNAs. The peptide library is encoded by nucleic acids. The effect of the candidate therapeutic agent on TGFβ2 expression or the acylation/deacetylation state of an enhancer element of TGFβ2, is then monitored. The effect of the agent can be validated and distinguished from somatic mutations, using, e.g., regulatable expression of the nucleic acid such as expression from a tetracycline promoter.

Proteins interacting with the peptide or with the protein encoded by the cDNA (e.g., distal enhancers) can be isolated using a yeast two-hybrid system, mammalian two hybrid system, or phage display screen, etc. Targets so identified can be further used as bait in these assays to identify additional members of the TGFβ2 regulatable pathways, which members are also targets for drug development (see, e.g., Fields et al., Nature 340:245 (1989); Vasavada et al., Proc. Nat'l Acad. Sci. USA 88:10686 (1991); Fearon et al., Proc. Nat'l Acad. Sci. USA 89:7958 (1992); Dang et al., Mol. Cell. Biol. 11:954 (1991); Chien et al., Proc. Nat'l Acad. Sci. USA 9578 (1991); and U.S. Pat. Nos. 5,283,173, 5,667,973, 5,468,614, 5,525,490, and 5,637,463).

In a preferred embodiment, a method of identifying therapeutic agents comprises contacting: (i) a peptide encoded by enhancer nucleic acid sequences, an active fragment, variant, or mutant thereof; or, (ii) nucleic acid sequences encoding distal enhancers, an active fragment, variant, or mutant thereof, with a candidate therapeutic agent; determining whether (i) the agent modulates expression of TGFβ2; and/or (ii) the agent modulates expression and/or function of distal enhancers; and/or (iii) the agent modulates of the acylation/deacetylation state of an enhancer element of TGFβ2; and/or (iv) BRD4 activity; and/or NF-κB activity or any combination thereof.

In another preferred embodiment, a method of identifying candidate therapeutic agents for treatment of disease, comprises culturing an isolated cell expressing TGFβ2 and/or distal enhancer nucleic acid sequences; administering a candidate therapeutic agent to the cultured cell; correlating TGFβ2 expression and/or enhancer function and/or acylation/deacetylation state of an enhancer element of TGFβ2 in the presence or absence of a candidate therapeutic agent as compared to control cells, wherein a drug is identified based on desirable therapeutic outcomes.

Another suitable method for diagnosis and candidate drug discovery includes contacting a test sample with a cell expressing enhancer sequences, TGFβ2, an allele or fragment thereof; and detecting interaction of the test sample with distal enhancer, an allele or fragment thereof, and/or expression of TGFβ2, an allele or fragment thereof, and/or acylation/deacetylation state of an enhancer element of TGFβ2. TGFβ2 and/or enhancer nucleic acid sequences, an allele or fragment thereof, or expression product of the TGFβ2 and/or enhancer gene, an allele or fragment thereof suitably can be detectably labeled e.g. with a fluorescent or radioactive component.

In another preferred embodiment, a cell from a patient is isolated and contacted with a candidate therapeutic molecule. The genes, expression products thereof, are monitored to identify which genes or expression products are regulated by the drug.

Nucleic Acid Microarrays: Identification of a nucleic acid sequence capable of binding to a distal enhancer can be achieved by immobilizing a library of nucleic acids onto the substrate surface so that each unique nucleic acid is located at a defined position to form an array. In general, the immobilized library of nucleic acids is exposed to a biomolecule or candidate agent under conditions which favored binding of the biomolecule to the nucleic acids. Nonspecifically binding biomolecules could be washed away using mild to stringent buffer conditions depending on the level of specificity of binding desired. The nucleic acid array would then be analyzed to determine which nucleic acid sequences bound to the biomolecule. Preferably the biomolecules would carry a fluorescent tag for use in detection of the location of the bound nucleic acids. These molecules can then also be cross-tested in one or more assays to determine TGFβ2 expression and/or enhancer function and/or acylation/deacetylation state of an enhancer element of TGFβ2 and/or BRD4 activity; and/or NF-κB activity or any combination thereof.

An assay using an immobilized array of nucleic acid sequences may be used for determining the sequence of an unknown nucleic acid; single nucleotide polymorphism (SNP) analysis; analysis of gene expression patterns from a particular species, tissue, cell type, etc.; gene identification; etc.

Additional diagnostic uses for oligonucleotides designed from the sequences encoding a desired gene expression product may involve the use of PCR. These oligomers may be chemically synthesized, generated enzymatically, or produced in vitro. Oligomers will preferably contain a fragment of a polynucleotide encoding the expression products, or a fragment of a polynucleotide complementary to the polynucleotides, and will be employed under optimized conditions for identification of a specific gene. Oligomers may also be employed under less stringent conditions for detection or quantitation of closely-related DNA or RNA sequences.

In further embodiments, oligonucleotides or longer fragments derived from any of the polynucleotide sequences, may be used as targets in a microarray. The microarray can be used to monitor the identity and/or expression level of TGFβ2 and/or enhancer sequences, genes and gene transcripts simultaneously to identify any other genes with which target genes or its product interacts and/or to assess the efficacy of candidate therapeutic agents in regulating expression products of genes that mediate, for example, TGFβ2-associated diseases or disorders.

Microarrays may be prepared, used, and analyzed using methods known in the art (see, e.g., Brennan et al., 1995, U.S. Pat. No. 5,474,796; Schena et al., 1996, *Proc. Natl. Acad. Sci. U.S.A.* 93: 10614-10619; Baldeschweiler et al., 1995, PCT application WO95/251116; Shalon, et al., 1995, PCT application WO95/35505; Heller et al., 1997, *Proc. Natl. Acad. Sci. U.S.A.* 94: 2150-2155; and Heller et al., 1997, U.S. Pat. No. 5,605,662). In other embodiments, a microarray comprises peptides, or other desired molecules which can be assayed to identify a candidate agent.

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Screening of therapeutic agent assays of the invention suitably include, animal models, cell-based systems and non-cell based systems. Details of some exemplary assays are described in the "Examples" section which follows. Preferably, identified genes, variants, fragments, or oligopeptides thereof are used for identifying agents of therapeutic interest, e.g. by screening libraries of compounds or otherwise identifying compounds of interest by any of a variety of drug screening or analysis techniques. The gene, allele, fragment, or oligopeptide thereof employed in such screening may be free in solution, affixed to a solid support, borne on a cell surface, or located intracellularly.

Another technique for drug screening provides for high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with identified genes, or fragments thereof, and washed. Bound molecules are then detected by methods well known in the art. Alternatively, non-neutralizing antibodies can be used to capture the peptide and immobilize it on a solid support.

The methods of screening of the invention comprise using screening assays to identify, from a library of diverse molecules, one or more compounds having a desired activity e.g. acylation/deacetylation state of an enhancer element of TGFβ2. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with isolated cells with modulated receptors, including the appropriate controls.

In one embodiment, screening comprises contacting each cell culture with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

In one embodiment the invention provides soluble assays using a TGFβ2 and/or enhancer nucleic acid sequence or product thereof, or a cell or tissue expressing a TGFβ2 protein, either naturally occurring or recombinant. In another embodiment, the invention provides solid phase based in vitro assays in a high throughput format, where the enhancer nucleic acid sequence and/or product and/or fragment thereof, is attached to a solid phase substrate. Any one of the assays described herein can be adapted for high throughput screening, e.g., ligand binding, TGFβ2 expression, enhancer function, acylation/deacetylation state of an enhancer element of TGFβ2, TGFβ2 cell surface marker flux, radiolabeled ligand binding, second messenger flux, e.g., Ca', cytokine production, etc.

In the high throughput assays of the invention, either soluble or solid state, it is possible to screen up to several thousand different modulators or ligands in a single day. This methodology can be used for proteins in vitro, or for cell-based or membrane-based assays. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non-covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder. A number of tags and tag binders can be used, based upon known molecular interactions well described in the literature. Similarly, any haptenic or antigenic compound can be used in combination with an appropriate antibody to form a tag/tag binder pair. Thousands of specific antibodies are commercially available and many additional antibodies are described in the literature Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinatorial chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA*. 91:10779-85, 1994; Lebl et al., One-bead-one-structure combinatorial libraries, *Biopolymers* 37:177-98, 1995; Eichler et al., *Peptide,* peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA,* 90:6909-6913 (1993)); vinylogous polypeptides (Hagihara, et al., *J. Amer. Chem. Soc.* 114:6568 (1992)); nonpeptidal peptidomimetics with .beta.-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd., Moscow, RU, 3D Pharmaceuticals, Exton, Pa., Martek Bio sciences, Columbia, Md., etc.).

High throughput screening can be used to measure the effects of drugs on complex molecular events, e.g. regulation of TGFβ2 expression by one or a multitude of enhancer molecules and/or enhancer function and/or acylation/deacetylation state of an enhancer element of TGFβ2. Multicolor fluorescence permits multiple targets and cell processes to be assayed in a single screen. Cross-correlation of cellular responses will yield a wealth of information required for target validation and lead optimization.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

This method relies on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids, RNA and DNA hybridizing probes. Similarly, fluorescent reagents specifically synthesized with particular chemical properties of binding or association have been used as fluorescent reporter molecules (Barak et al., (1997), *J. Biol. Chem.* 272:27497-27500; Southwick et al., (1990), *Cytometry* 11:418-430; Tsien (1989) in *Methods in Cell Biology,* Vol. 29 Taylor and Wang (eds.), pp. 127-156). Fluorescently labeled antibodies are particularly useful reporter molecules due to their high degree of specificity for attaching to a single molecular target in a mixture of molecules as complex as a cell or tissue. The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17-20; Bright et al. (1996), *Cytometry* 24:226-233; McNeil (1989) in *Methods in Cell Biology,* Vol. 29, Taylor and Wang (eds.), pp. 153-173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448-455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405-434; Giuliano and Taylor (1995), *Methods in Neuroscience* 27.1-16). The pH environment of the reporter can be determined (Bright et al. (1989), *J. Cell Biology* 104:1019-1033; Giuliano et al. (1987), *Anal. Biochem.* 167:362-371; Thomas et al. (1979), *Biochemistry* 18:2210-2218). It can be determined whether a reporter having a chelating group is bound to an ion, such as $Ca^{++}$, or not (Bright et al. (1989), In *Methods in Cell Biology*, Vol. 30, Taylor and Wang (eds.), pp. 157-192; Shimoura et al. (1988), *J. of Biochemistry* (Tokyo) 251:405-410; Tsien (1989) In *Methods in Cell Biology*, Vol. 30, Taylor and Wang (eds.), pp. 127-156).

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405-434; Giuliano et al. (1995), *Methods in Neuroscience* 27:1-16).

The whole procedure can be fully automated. For example, sampling of sample materials may be accomplished with a plurality of steps, which include withdrawing a sample from a sample container and delivering at least a portion of the withdrawn sample to test cell culture (e.g., a cell culture wherein gene expression is regulated). Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

Labels: The particular label or detectable moiety or tag used in the assay is not a critical aspect of the invention. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical, or chemical means.

Useful labels in the present invention include magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Any type of enzyme label can be used as long as they do not interfere with one of the desired outputs of the assay, e.g. TGFβ2 expression and/or enhancer function and/or acylation/deacetylation state of an enhancer element of TGFβ2 Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Methods of Treatment

As used herein, the term "TGFβ2-associated disease, disorder and/or condition" is intended to mean any disease, disorder and/or condition that has been identified or may be identified as associated with altered expression and/or activity of TGFβ2. Exemplary TGFβ2-associated diseases, disorders and/or conditions of the instant disclosure include those associated with upregulation of TGFβ2 (optionally induced by distal enhancer sequence(s) of TGFβ2), such as Scleroderma, other fibrotic disease, grade 4 glioblastoma (GBM) and/or Primary Open-Angle Glaucoma (POAG).

The term "treated," "treating" or "treatment" includes the diminishment or alleviation of at least one symptom associated or caused by a TGFβ2-associated disease, disorder and/or condition. For example, treatment can be diminishment of one or several symptoms of a disease or disorder or complete eradication of the disease or disorder, e.g., Scleroderma.

The term "subject" is intended to include organisms, e.g., eukaryotes, which are capable of suffering from or afflicted with a TGFβ2-associated disease, disorder and/or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a TGFβ2-associated disease, disorder and/or condition.

The agents and pharmaceutical compositions of the disclosure can be administered to a subject to treat or prevent diseases, disorders and conditions associated with aberrant expression or activity of TGFβ2. In one embodiment, the agents and pharmaceutical compositions are used to treat or prevent Scleroderma, other fibrotic diseases, or other diseases or disorders associated with aberrant TGFβ2 expression.

In one embodiment, the agents or pharmaceutical compositions are administered in an effective amount using a dosing schedule determined by a medical provider to treat or prevent a disease or disorder set forth herein. The agents or pharmaceutical compositions can be administered in a variety of methods, as described herein and known to one of skill in the art.

In one aspect, the disclosure provides a method for treating or preventing in a subject, a disease or condition associated with aberrant expression or activity of TGFβ2, or a gene product thereof, by administering to the subject an agent which modulates an enhancer of TGFβ2. Subjects at risk for a disease which is caused or contributed to by aberrant expression or activity of TGFβ2, or a gene product thereof, can be identified by, for example, any or a combination of diagnostic or prognostic assays as described herein.

Administration of a prophylactic agent can occur prior to the manifestation of symptoms characteristic of the aberrancy of expression or activity of TGFβ2, such that a disease or disorder is prevented or, alternatively, delayed in its progression.

Another aspect of the disclosure pertains to methods of modulating expression or activity of a regulator of TGFβ2 enhancer sequence acylation, for therapeutic purposes. Accordingly, in an exemplary embodiment, the modulatory method of the disclosure involves contacting a cell with an agent that modulates one or more of the activities of a TGFβ2 enhancer sequence. An agent that modulates expression or activity of TGFβ2 can be an agent as described herein, such as a small molecule, nucleic acid or polypeptide. In one embodiment, the agent inhibits one or more activities of TGFβ2 and/or a TGFβ2 enhancer sequence, and/or inhibits one or more components of the TGFβ2 (acylation) pathway. Examples of such inhibitory agents include antisense P300 nucleic acid molecules, anti-P300 antibodies, and small molecule inhibitors of acylases and/or small molecule and/or enzyme activators of deacetylation at the TGFβ2 enhancer sequence. These modulatory methods can be performed in vitro (e.g., by culturing the cell with the agent) or, alternatively, in vivo (e.g., by administering the agent to a subject). As such, the present disclosure provides methods of treating an individual afflicted with a disease or disorder characterized by aberrant TGFβ2 expression, e.g., Scleroderma, other fibrotic diseases grade 4 glioblastoma (GBM) and/or Primary Open-Angle Glaucoma (POAG). In one embodiment, the method involves administering an agent, or combination of agents that modulates TGFβ2 signaling.

The disclosure further provides kits comprising agents or pharmaceutical compositions of the disclosure and instructions for use. In one embodiment, the kits of the disclosure are for the treatment of diseases and disorders characterized by aberrant TGFβ2 signaling. In a related embodiment, the TGFβ2 signaling associated disease or disorder is Scleroderma, other fibrotic diseases grade 4 glioblastoma (GBM) and/or Primary Open-Angle Glaucoma (POAG).

Pharmaceutical Compositions of the Invention

The agents described herein can be formulated into pharmaceutical compositions for the treatment of the diseases, disorders and conditions disclosed herein. The language "pharmaceutical composition" includes preparations suitable for administration to mammals, e.g., humans. When the compounds used in the methods of the present disclosure are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other nontoxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (13HT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue, The preparations of the present disclosure may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above. Generally, intravenous and subcutaneous doses of the compounds of this disclosure for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day.

An effective amount is that amount treats a disease, disorder or condition set forth herein.

If desired, the effective daily dose of the active compound may be administered as two, three, four, five, six or more sub-doses administered separately at appropriate intervals throughout the day, optionally, in unit dosage forms.

While it is possible for a compound of the present disclosure to be administered alone, it is preferable to administer the compound as a pharmaceutical composition.

Certain aspects of the disclosure involve administration of nucleic acid agents. Nucleic acid agents can be effectively delivered to a subject as stabilized agents, with such stability often provided via lipid nanoparticle (LNP) encasement of active nucleic acid agents and/or modification of therapeutic nucleic acid agents with one or more stabilizing modifications, including, e.g., 2'-O-alkyl modifications (including 2'-O-methyl), 2'-F modifications, backbone modifications, locked nucleic acid (LNA) configurations, GalNAc modifications, cholesterol conjugates, etc. Such modifications are known in the art and can be readily employed by the skilled artisan for delivery of the nucleic acid agents of the instant disclosure.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

It should be appreciated that the invention should not be construed to be limited to the examples that are now described; rather, the invention should be construed to include any and all applications provided herein and all equivalent variations within the skill of the ordinary artisan.

Example 1: Targeted Epigenetic Therapy Against Distal Regulatory Element of TGFβ2 Expression for Scleroderma and Fibrotic Disease Systemic Sclerosis (SSc) is a rare and complex disorder characterized by adult-onset predisposition for progressive fibrosis of the skin and viscera with high mortality. Disease associates with an overt inflammatory prodrome and sustained auto-inflammation, but it is unclear if this is a marker or driver of disease. In the absence of a strong genetic signature in twin studies (monozygous=dizygous=4% concordance) or GWAS (only indicative of inflammatory predisposition), there are few pathogenic insights and no specific treatment for SSc.

Lesional skin of Scleroderma patients has consistently been associated with heightened levels of transforming growth factor β (TGFβ) signaling in dermal fibroblasts. Elevated TGFβ signaling is sufficient to drive dermal fibrosis, as evidenced in various animal models of fibrosis (Sonnylal S et al. (2007). *Arthritis and Rheumatism.* 56:334-344). In line with prior literature, it was previously observed that primary SSc fibroblasts maintain higher expression of TGFβ target genes, such as type 1 collagen, when cultured ex vivo under serum-deprived conditions (Gerber E E et al. (2013). *Nature.* 503:126-130). These results suggested that SSc fibroblasts maintain a pro-fibrotic synthetic repertoire ex vivo. However, large-scale genomic and exomic screens of SSc patients have not identified genomic variants with clear biological function (Murdaca G (2016). *Autoimmunity Reviews.* 15:427-432). Therefore, it remains unclear how SSc fibroblasts can stably maintain pro-fibrotic transcriptomic differences ex vivo. This question, if solved, will significantly advance our understanding of the etiology of Scleroderma, and help to identify therapeutic targets for Scleroderma and many fibrotic diseases driven by TGFβ.

The observation that the Scleroderma concordance rate of monozygotic twins is merely 4%, comparable to that of dizygotic twins (Feghali-Bostwick C et al. (2003). *Arthritis and Rheumatism.* 48:1956-1963), indicated that genetic variation cannot solely account for Scleroderma etiology. Given that epigenetic programs integrate environmental as well as genetic factors and can cause stable dysregulation of gene expression without alterations to the genome, it was hypothesized that SSc fibroblasts are locked into an epigenetic landscape that drives the expression of pro-fibrotic genes.

To test this hypothesis, it was first validated whether primary dermal SSc fibroblast lines established from dermal biopsies maintained stable gene expression differences at baseline. Six dermal fibroblasts lines from SSc patients and five dermal fibroblast lines from healthy controls were cultured in serum-deprived conditions (DMEM+1% FCS) for 48 hours, followed by mRNA isolation. RNAseq analysis indicated significant transcriptomic differences (FDR<0.05) with heightened expression of extracellular matrix genes (P<1E-9) in SSc fibroblasts (FIG. 1A). By RT-qPCR, elevated expression of pro-fibrotic genes, such as COL1A1 and SERPINH1 (FIG. 1B), were independently validated. TGFβ expression, the dominant pro-fibrotic cytokine, was also assessed. SSc fibroblasts expressed 4-fold higher mRNA and 2-fold higher protein levels of TGFβ2 ligand specifically, but not TGFβ1 or TGFβ3 (FIGS. 1C, 1D). This indicated transcriptional upregulation of TGFβ2 in SSc fibroblasts. Taken together, these data demonstrate that SSc fibroblasts maintain a fibrotic synthetic repertoire ex vivo. Informatively, no differences were observed in ACTA2 mRNA levels between control and SSc fibroblasts. Since ACTA2 is a marker for myofibroblast differentiation, this indicated that changes in gene expression in SSc fibroblasts likely reflect differences in cellular performance than cellular state.

Figure 8:
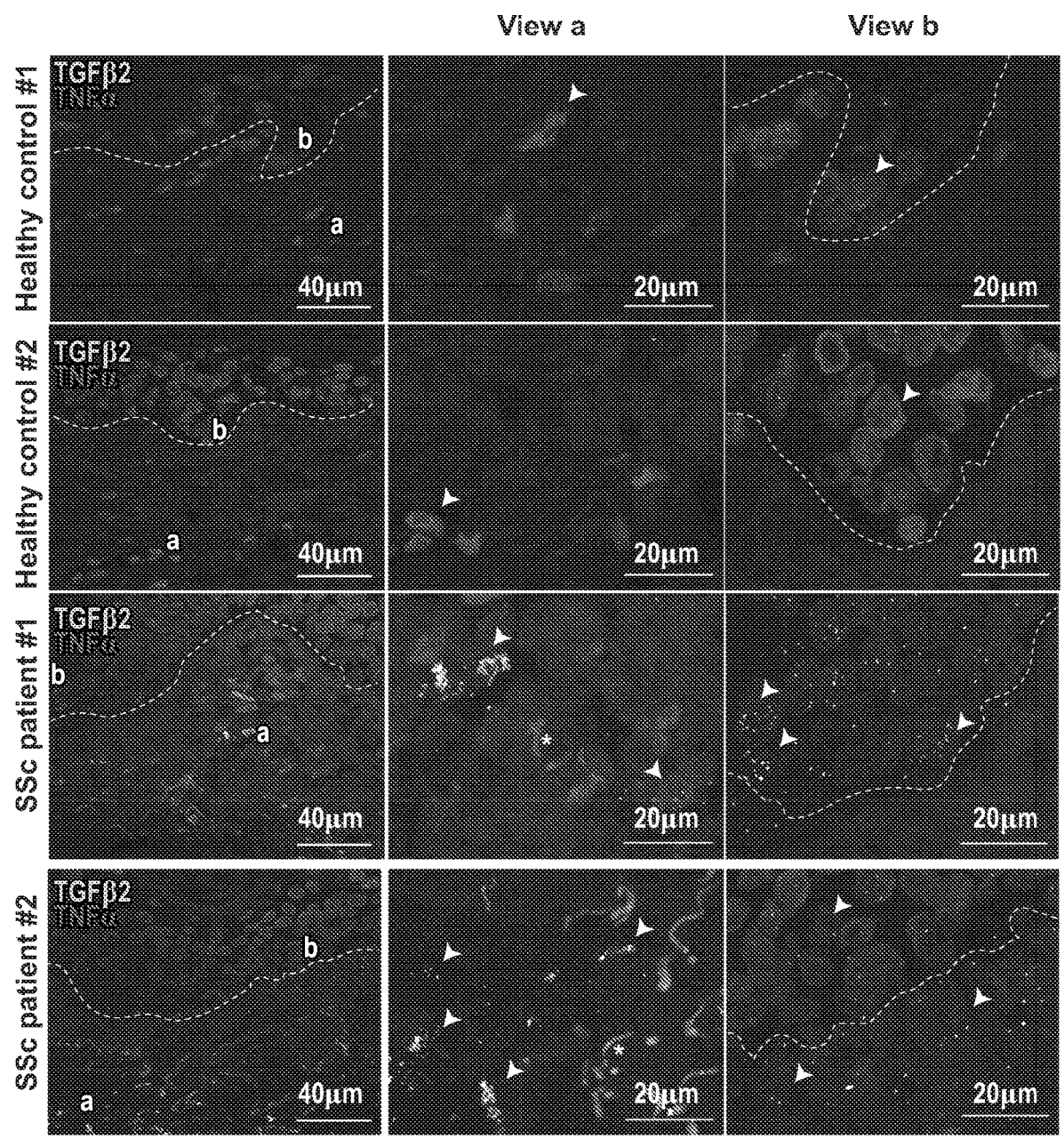
FIG. 8 shows that SSc lesional skin exhibits high TGFB2 and TNFA expression. RNA in situ hybridization study indicates significant enrichment of TGFB2 (green) and TNFA (red) expression in lesional skin of SSc patients. First column shows representative images of 40× images. Particular regions (indicated by a or b) have been magnified and displayed in adjacent images. Arrows highlight cells with TGFB2 expression. Dashed lines indicate epidermal-dermal junction. Asterisks indicate autofluorescent collagen fibers. N=2.

Consistent with ex vivo studies, lesional skins of SSc patients were significantly enriched for cells that express TGFB2 in both dermal and epidermal layers, unlike healthy controls. Furthermore, lesional skins were associated with high expression of TNFA, a potent pro-inflammatory cytokine (FIG. 8). This result attested to the particular pathogenic importance of TGFβ2, and indicated that SSc fibroblasts maintain their in vivo pro-fibrotic gene expression ex vivo.

It was found that heightened levels of COL1A1 and TGFβ2 expression in SSc fibroblasts were prone to further amplification by TGFβ2 (FIGS. 1D, 1F). This provided evidence that autocrine TGFβ2 signaling drives high collagen expression in SSc. To test this, the activity of ALK5, a TGFβ receptor kinase required by all TGFβ isoforms, was inhibited. ALK5 inhibition normalized collagen expression in SSc fibroblasts (FIG. 1E, P<0.05). Interestingly, treatment with neutralizing antibodies that specifically block TGFβ2 signaling activity (αTGFβ2ab) achieved equivalent suppression of collagen expression as that of ALK5 inhibition in SSc fibroblasts (FIG. 1E, P<0.05). The comparable magnitude of decrease in collagen expression after ALK5 inhibition (31%) or anti-TGFβ2 antibody treatment (25%) indicated that heightened collagen expression in SSc fibroblasts is likely secondary to heightened signaling by TGFβ2 ligand.

Figure 5:
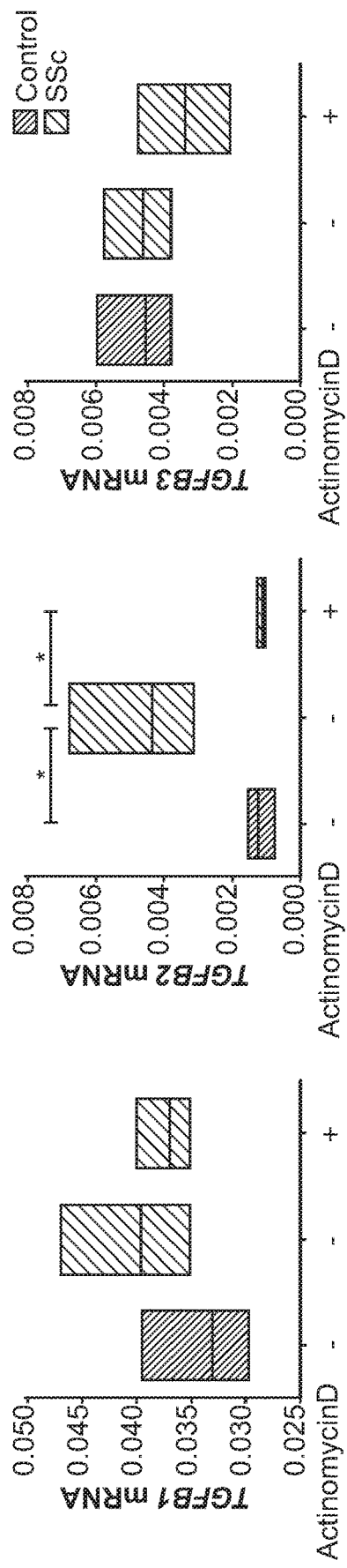
FIG. 5 shows the active transcription rates of TGF isoforms assessed through treatment of control and SSc fibroblasts with actinomycin D.

Since heightened TGFβ2 signaling drives collagen expression in SSc cells, the possible mechanisms of heightened TGFβ2 ligand expression in SSc fibroblasts, was investigated. First, it was determined if SSc fibroblasts were actively transcribing TGFβ2 mRNA by treating SSc or control fibroblasts with the transcriptional inhibitor actinomycin D for 12 hours, followed by mRNA isolation and RT-qPCR. Whereas actinomycin D treatment did not significantly alter levels of TGFβ1 or TGFβ3 mRNA expression, it completely normalized the level of TGFβ2 mRNA expression in SSc fibroblasts to levels comparable to controls (FIG. 5, P<0.05). This indicated that SSc fibroblasts maintained higher TGFβ2 ligand expression through higher promoter activity.

Second, it was determined if autocrine TGFβ2 signaling drives the steady-state differences in TGFβ2 mRNA expression in SSc fibroblasts. Cells were treated with isotype control or αTGFβ2ab in the presence or absence of saturating levels of exogenous TGFβ2 ligand (10 ng/mL), followed by mRNA isolation and RT-qPCR. Upon exogenous TGFβ2 ligand treatment, SSc fibroblasts showed a pronounced further increase in TGFβ2 mRNA (P<0.05) that was abrogated in cells that were co-treated with neutralizing anti-TGFβ2 antibody. Interestingly, SSc fibroblasts that were treated with αTGFβ2ab in the absence of exogenous ligand continued to show higher TGFβ2 mRNA expression than controls (P<0.01), equivalent to that observed under basal conditions. This indicated that elevated baseline levels of TGFβ2 is likely not due to autocrine TGFβ2 signaling.

Figure 1G:
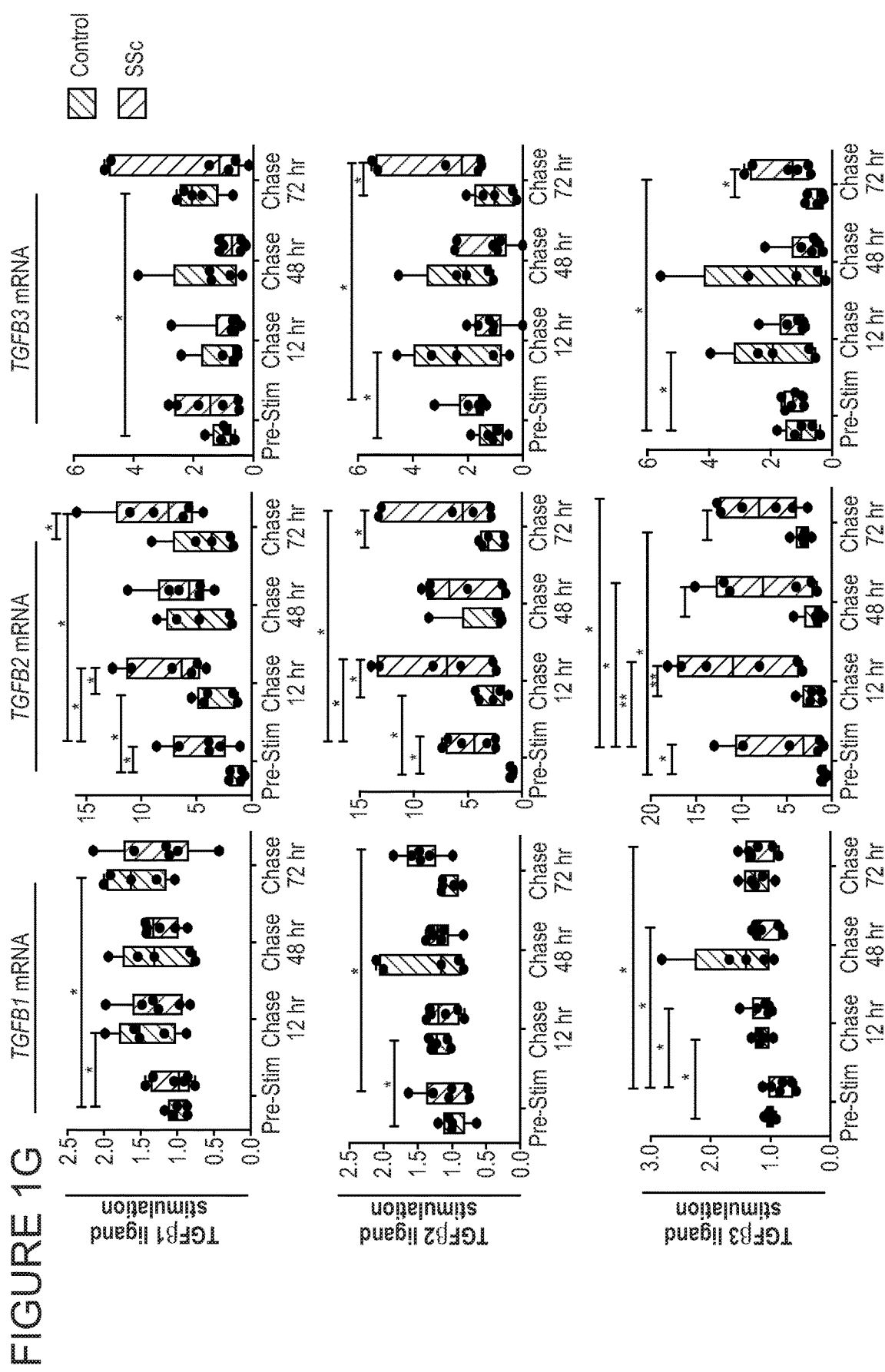
FIG. 1G: mRNA expression kinetics of TGF isoforms upon acute TGF ligand stimulation was assessed by pulsing control or SSc cells with TGFβ1 (long/mL), TGFβ2 (long/mL), or TGFβ3 (long/mL) for 12 hours, after which cells were incubated in fresh serum-deprived media for the following 12, 48, 72 hours post-stimulation.

Third, since exogenous TGFβ2 ligand further amplifies TGFβ2 expression in SSc fibroblasts, it was queried as to whether SSc fibroblasts can sustain high TGFβ2 mRNA levels over time. To test this, SSc or control fibroblasts were acutely pulsed with exogenous TGFβ1, TGFβ2, or TGFβ3 ligand for 12 hours, after which time point the ligands were washed out with fresh serum-deprived media. mRNA was isolated either before ligand stimulation or at 12, 48 or 72 hour post-stimulation, and assayed by RT-qPCR. SSc and control fibroblasts induced TGFβ1 or TGFβ3 expression upon exogenous TGFβ2 ligand treatment at comparable levels (FIG. 1G). Interestingly, SSc fibroblasts induced and maintained much higher expression of TGFβ2 mRNA up to 72 hours after ligand stimulation (P<0.05). Similar results were observed when cells were treated with exogenous TGFβ1 or TGFβ3. These data document the potential for an autocrine feed-forward mechanism for fibrosis in SSc, but also demonstrate a baseline tendency for high TGFβ2 mRNA transcription. This would be consistent with a generalized accessible chromatin state at the TGFβ2 locus that could respond to both TGFβ—(i.e. Smad-dependent) and Smad-independent transcriptional activation. Taken together, our data suggested that SSc fibroblasts contain unique chromatin accessible regions (ChARs) near the TGFβ2 locus that allows higher baseline expression of TGFβ2.

Figure 2A:
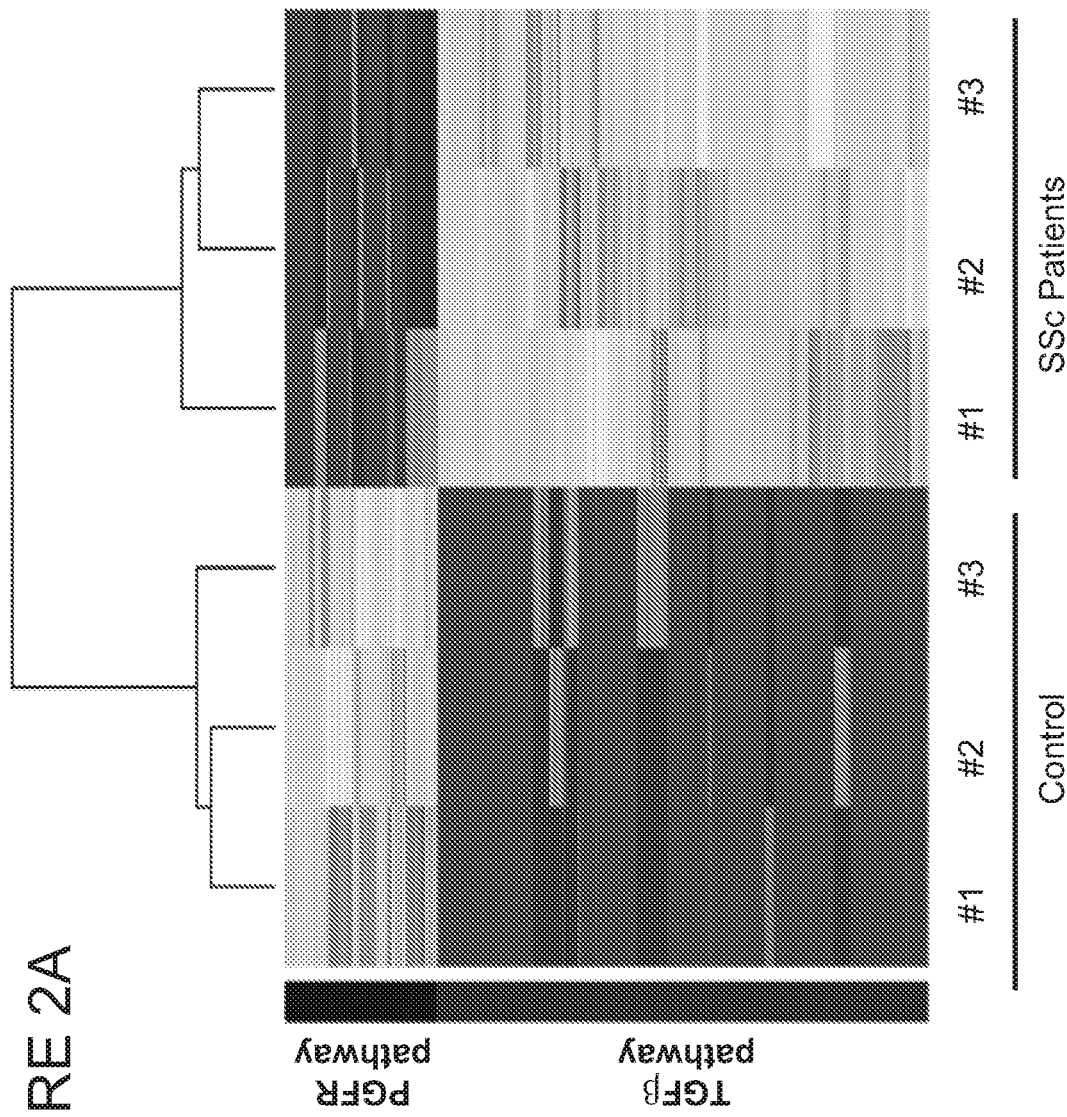
FIG. 2A is a heatmap. Unsupervised hierarchical clustering was performed on genes with significant chromatin accessibility (FDR<0.01, log 2FC<|0.5|) assessed by ATAC-seq on primary control and SSc fibroblasts. Gene Ontology (GO) term analysis was performed on each gene cluster. Top ranking GO term result for each gene cluster is indicated on the left of the heatmap.

To test this hypothesis, an RNA-seq and Assay for Transposase-Accessible Chromatin Sequencing (ATAC-seq) were performed on three primary control fibroblast lines and three primary SSc fibroblast lines[7]. Unsupervised hierarchical clustering on genes with significantly different chromatin accessibility (FDR<0.01 and log 2FC>|0.5|) was performed. SSc samples clustered separately from controls (FIG. 2A), indicating significant differences in the epigenomic landscape in SSc fibroblasts. Furthermore, GO term analysis indicated that SSc cells exhibited increased chromatin accessibility at genes associated with TGFβ-activated receptor signaling (GO:0005024, P<5E-4) and TGFβ-binding (GO: 0050431, P<4E-4) compared to controls.

Figure 2B:
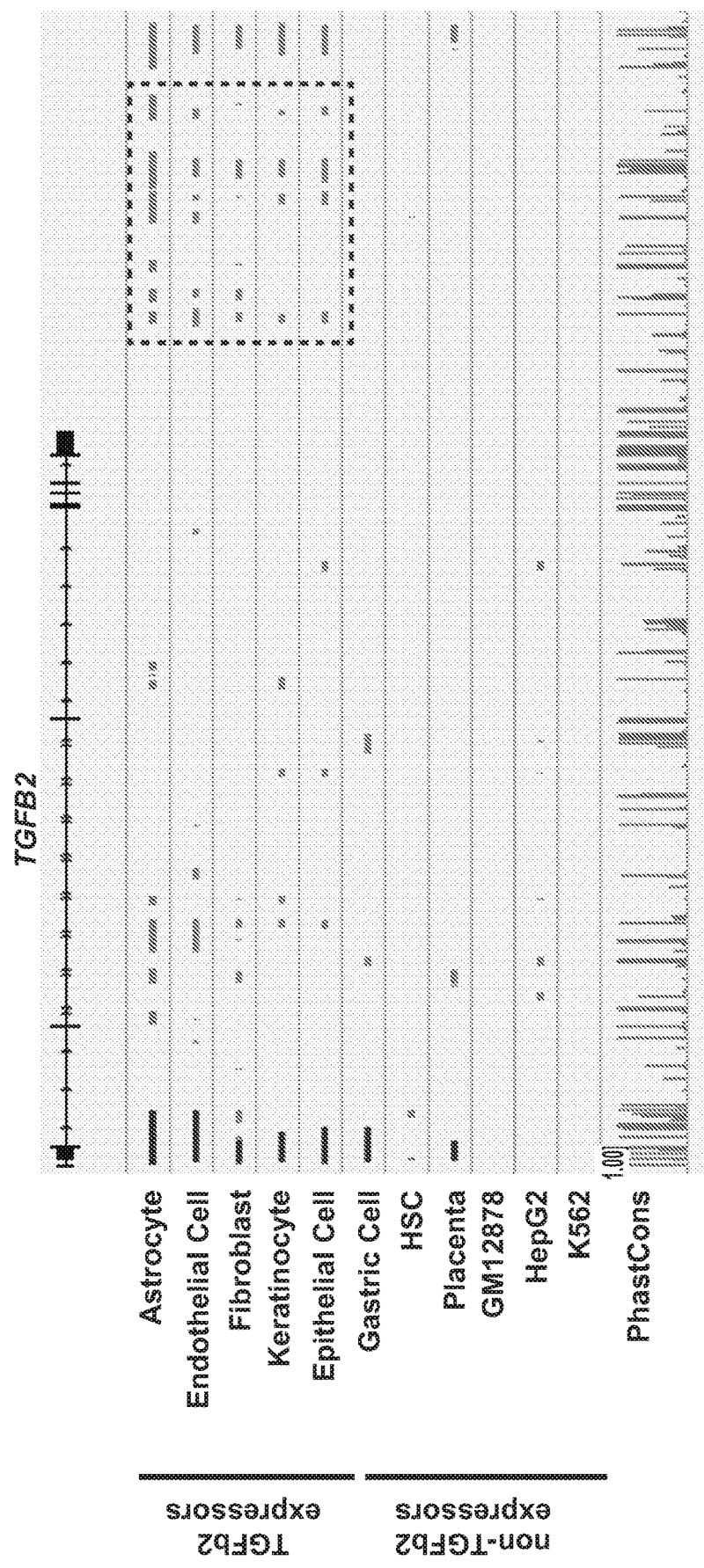
FIG. 2B: Annotated BED files containing predicted proximal promoter (red) and enhancer regions (green) of 10 cell lines are aligned at the TGFβ2 locus (from ENCODE). Cell lines were binned as "TGFβ2 expressors" or "non-TGFβ2 expressors" based on mRNA expression levels of TGFβ2 found in RNA-seq data of each cell line (threshold: 1 TPM).
Figure 2C:
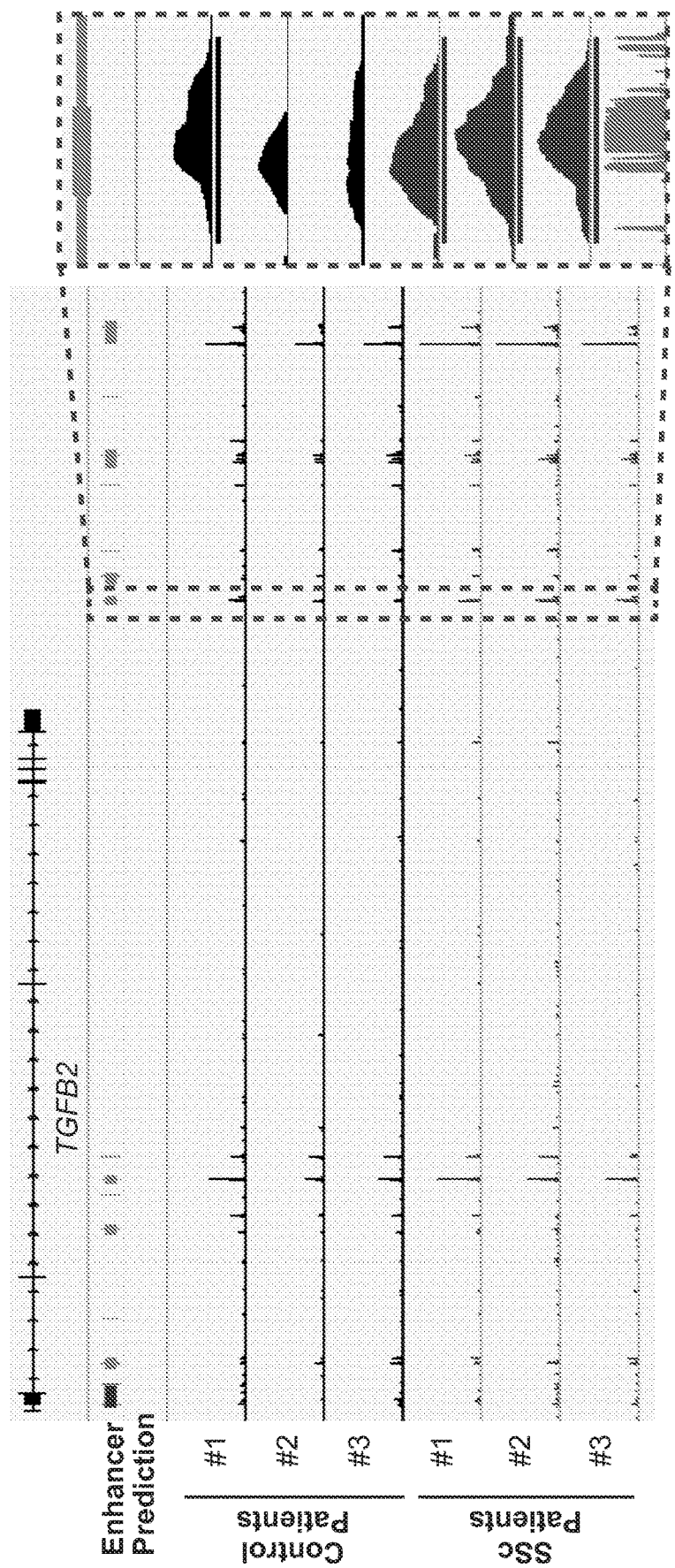
FIG. 2C: ATAC-seq tracks of control (blue) and SSc fibroblasts (red) at the TGFB2 locus (above), and annotated BED files for predicted proximal promoter (red) and enhancer (green) regions of adult lung fibroblasts (from ENCODE). Closer view of ATAC-seq tracks at candidate enhancer sequence with differential levels of accessibility between controls and SSc (right).

ChARs between control and SSc fibroblasts were compared, with reference to an annotation track from ENCODE, which predicts the presence of proximal promoter of enhancer sequences based on DNAse hypersensitivity, ChIP-seq, and sequence constraint. By visual inspection, no significant differences were observed in ChAR at the proximal promoter between control and SSc fibroblasts (FIG. 2c). Interestingly, there were over 10 different predicted enhancers within or adjacent to the TGFβ2 locus. To filter for biologically meaningful enhancers, we utilized annotated BED files that predicted proximal promoters and enhancer regions for 10 different cell lines, for which there were also RNA-seq profiles deposited in ENCODE (FIG. 2b). Cell lines that expressed more than 1 transcript per million for TGFβ2 were binned as "TGFβ2 expressors", and cell lines that expressed less than 1 transcript per million for TGFβ2 were binned as "non-TGFβ2 expressors". The list of predicted enhancer regions of TGFβ2 expressors were intersected with that of non-TGFβ2 expressors with the hypothesis that biologically meaningful enhancers involved in TGFβ2 expression would be enriched among TGFβ2 expressing cell lines.

Figure 2D:
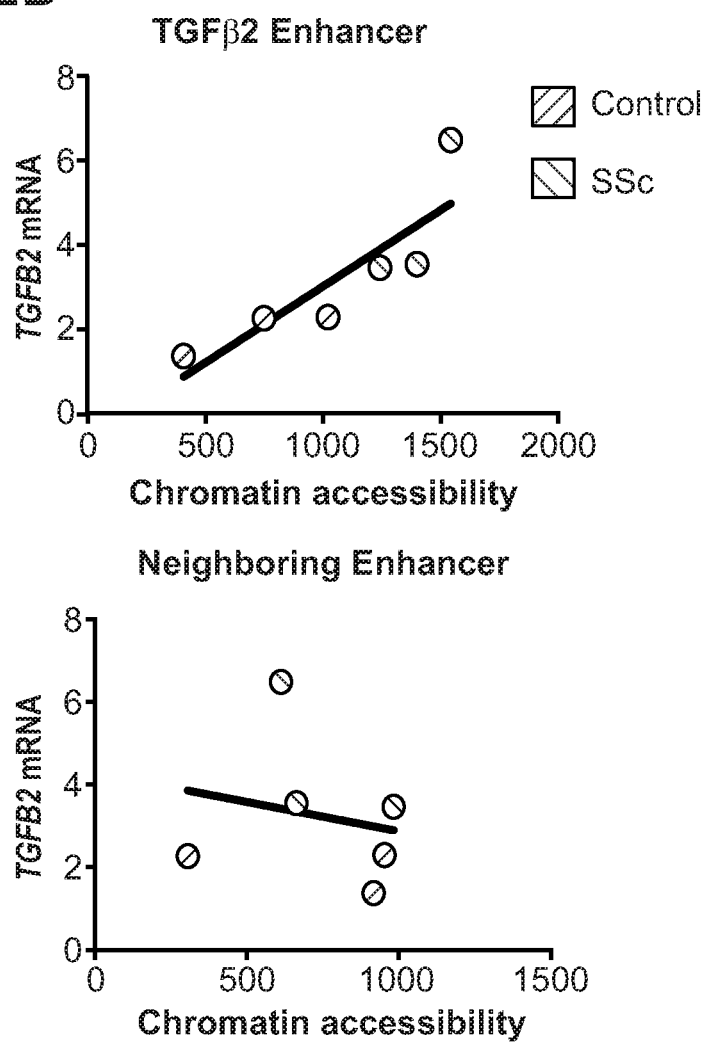
FIG. 2D: Correlation of chromatin accessibility at Enhancer 4514 or the neighboring enhancer with TGFβ2 expression measured by RNA-seq, which was performed in parallel with ATAC-seq.

Interestingly, a distal group of enhancers were found, located approximately 15 kb downstream of the TGFβ2 3'UTR that unequivocally showed a signature for open chromatin exclusively among TGFβ2 expressing cell lines (Distal Prediction 4514: chr1 218632917-218634115; Distal Prediction 7333: chr1 218649861-218650010; Distal Prediction 513: chr1 218652485-218655093; Distal Prediction 12430: chr1 218662521-218662670; hg19). Among this group, one enhancer (Distal Prediction 4514, or "Enhancer 4514") was identified that showed significantly higher chromatin accessibility in SSc fibroblasts than in controls (FIG. 2C, P=0.01). Using the MACS2 statistical package, it was determined that 3 of 3 SSc patient lines contained an epigenome-wide statistically significant ChAR at this enhancer (P=1E-30, P=1E-24, P=1E-27, respectively), whereas only 1 of 3 control patients contained a statistically significant ChAR at this enhancer (P=1E-18). Furthermore, it was observed that the degree of accessibility of Enhancer 4514 directly correlated with TGFβ2 mRNA expression in all samples tested (FIG. 2D, $R^2$=0.74, P=0.03), including controls. Similar analysis was performed using all 13 predicted enhancers that neighbor Enhancer 4514, but accessibility of neighboring enhancers did not correlate with TGFβ2 mRNA expression (FIG. 2D, $R^2$=0.04, P=0.7). Of important note, Enhancer 4514 contained binding motifs for defined transcription factors, 80% of which were shared with the proximal promoter of TGFβ2, including Smad2. Motifs unique to Enhancer 4514 included binding sites for DNA-binding factors known to regulate TGFβ target gene expression, such as SMARC1, NF-kB, Estrogen Related Receptor 1 (ERR1) (FIG. 3A). These in silico studies provided further evidence that the 6 to 1 higher incidence of scleroderma in females versus males might be associated with an influence of estrogen on enhancer 4514 via ERR1.

Figure 3B:
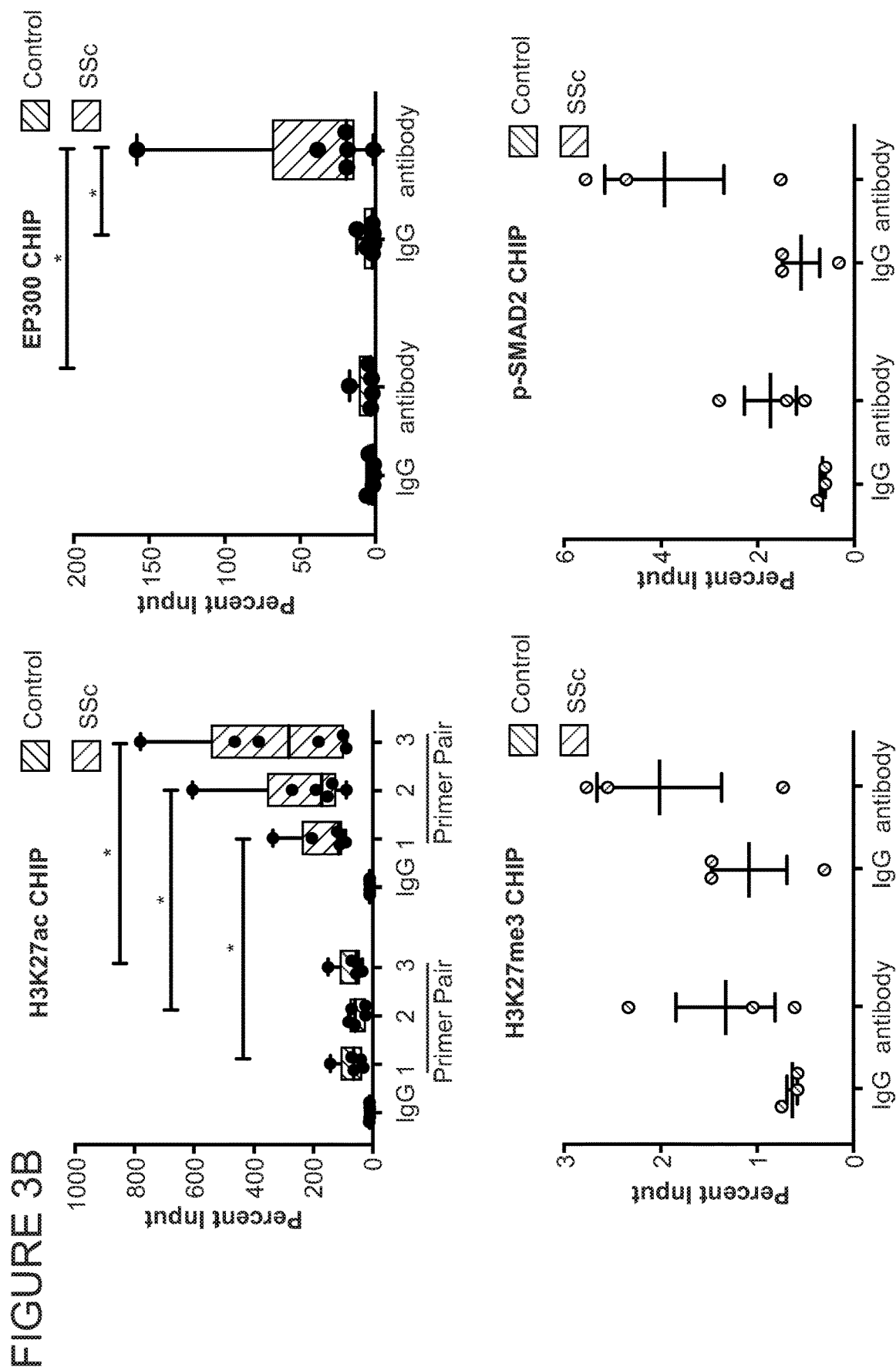
FIG. 3B: H3K27ac ChIP-qPCR was performed on control and SSc fibroblasts using primers targeted at three different locations of the enhancer. H3K27me3, P300 and p-SMAD2 ChIP-qPCR were also performed on control and SSc fibroblasts using primers targeted at Enhancer 4514.

To determine if Enhancer 4514 was biologically functional, a three-pronged approach was taken. First, active and functional enhancers are strongly associated with H3K27ac histone modifications with heightened occupancy of P300 (histone acetyltransferase) (Cato E et al. (2013) *Cell Molecular Cell Reviews.* 49:825-837). Thus, chromatin immunoprecipitation was used followed by qPCR (ChIP-qPCR) to determine the level of H3K27ac and P300 at Enhancer 4514 in SSc and control fibroblasts under baseline serum-deprived conditions. SSc fibroblasts exhibited significantly higher levels of H3K27ac and P300 occupancy at Enhancer 4514 compared to controls (FIG. 3B, P<0.05). Informatively, equivalent levels of the repressive mark H3K27me3 were observed in control and SSc fibroblasts. Furthermore, moderately higher levels of phosphorylated SMAD2 occupancy was found at enhancer 4514 in SSc. Collectively, these results provided evidence that in SSc fibroblasts, enhancer 4514 exhibits a signature for highly active and functional enhancers.

Figures 3C, 3D:
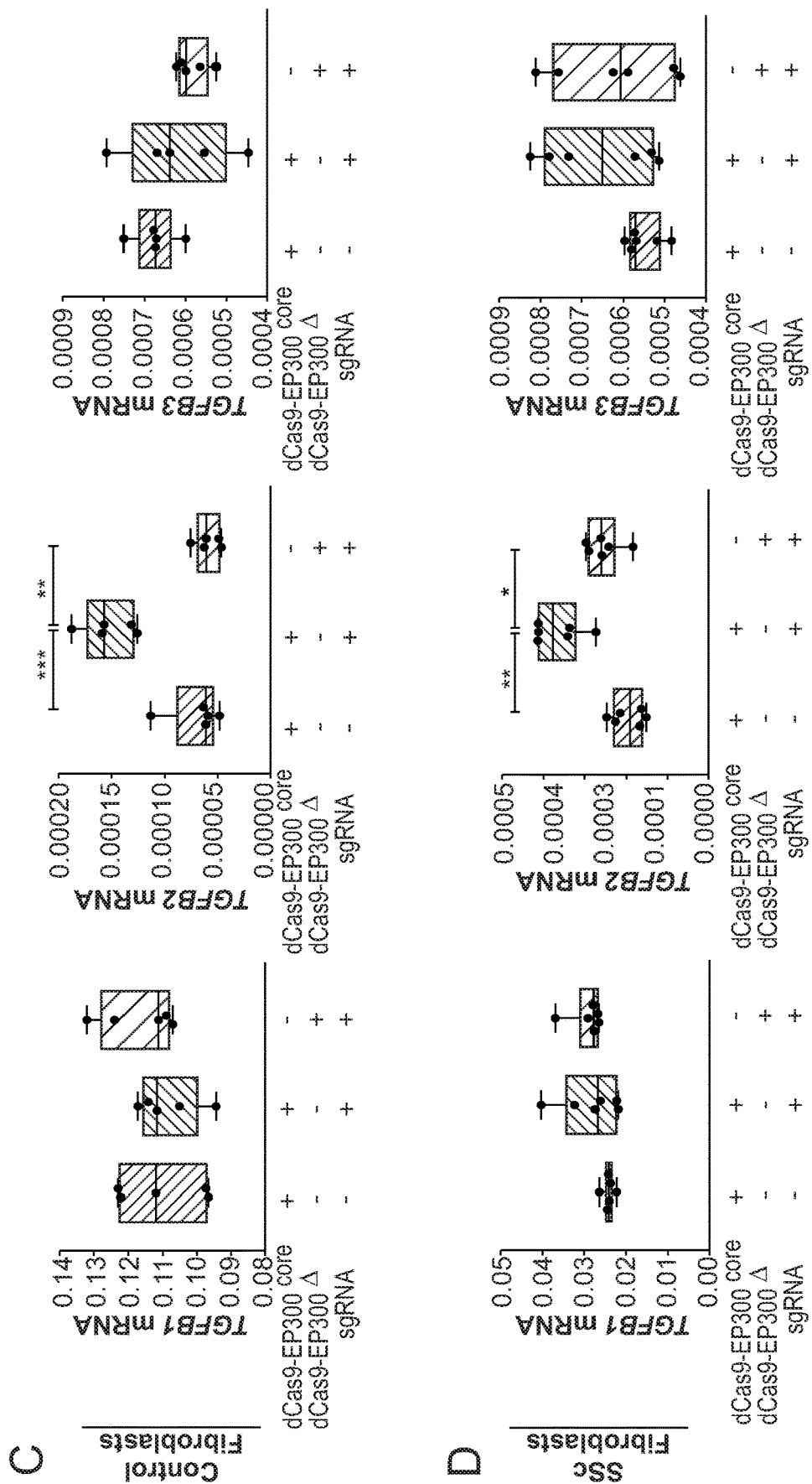
FIG. 3C: Effects of targeted epigenome editing was assessed by transfecting primary control
FIG. 3D: SSc fibroblasts with dCas9-EP300$^{core}$ only, dCas9-EP300$^{core}$ and sgRNA, or dCas9-EP300$^Δ$ and sgRNA expression constructs. mRNA transcript levels were measured 72 hours post-transfection by RT-qPCR. Five sgRNA constructs were designed to target dCas9-EP300 constructs to various regions of Enhancer 4514.
Figure 6:
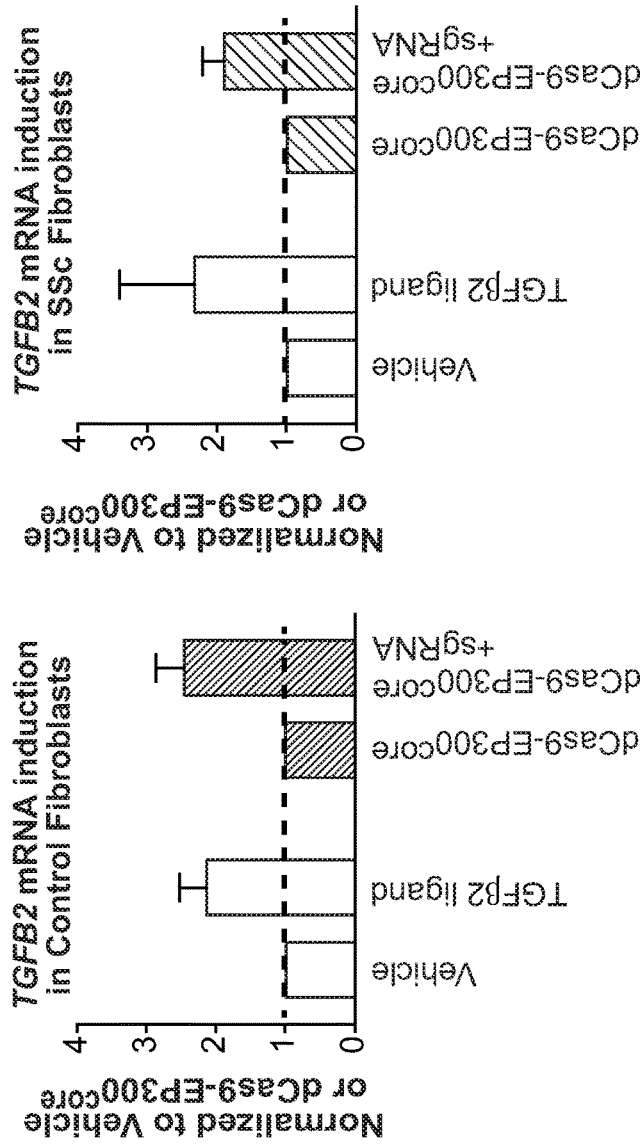
FIG. 6: To compare the level of TGFβ2 mRNA induction by dCas9-EP300core to that by TGFβ2 stimulation, TGFβ2 mRNA levels in fibroblasts transfected with dCas9-EP300$^{core}$ with sgRNA was normalized to level of TGFβ2 mRNA in cells transfected with dCas9-EP300$^{core}$ only. TGFβ2 mRNA in control or SSc fibroblasts stimulated with TGFβ2 ligand was normalized to TGFβ2 mRNA levels in vehicle-treated cells.

Second, targeted epigenome editing was performed to demonstrate the function of Enhancer 4514. To accomplish this, an expression construct was obtained (Gersbach lab) for a mutant, non-cleaving Cas9 that is tethered to the core acetyltransferase domain of P300 (dCas9-EP300$^{core}$), which specifically acetylates H3K27 and in turn activate targeted enhancers (Hilton I B (2014). *Nature.* 33:510-515). sgRNA constructs were designed to target dCas9-EP300$^{core}$ to the candidate enhancer. To control for non-specific effects of dCas9, cells were also transfected with dCas9-EP300$^{\Delta}$, which contains a loss-of-function mutation within the acetyltransferase domain. Informatively, co-transfection of dCas9-EP300$^{core}$ and sgRNA further specifically expressed significantly higher levels of TGFβ2 mRNA, when compared to controls transfected with dCas9-EP300$^{core}$ only or dCas9-EP300$^{\Delta}$ with sgRNA (FIGS. 3C, 3D, P<0.01). Furthermore, the magnitude of TGFβ2 mRNA induction by targeted activation of enhancer 4514 was comparable to the induction of TGFβ2 mRNA after TGFβ ligand stimulation (FIG. 6).

Histone methyltransferase activity was targeted to the putative enhancer using deactivated Cas9 tethered to a KRAB domain (a gift from Charles Gersbach lab), to repress TGFβ2 expression. Targeted methylation of the putative enhancer normalized TGFβ2 expression in SSc fibroblasts (FIG. 3E). Furthermore, epigenetic repression of the putative TGFβ2 enhancer concomitantly normalized TGFβ-target gene expression in SSc fibroblasts. These results demonstrate that epigenetic modifications that activate the TGFβ2 enhancer contribute to the maintenance of pro-fibrotic synthetic repertoire in SSc fibroblasts. Taken together, these data validate the function of Enhancer 4514 as a potent regulator of TGFβ2 expression.

Figures 4A, 4B, 4C:
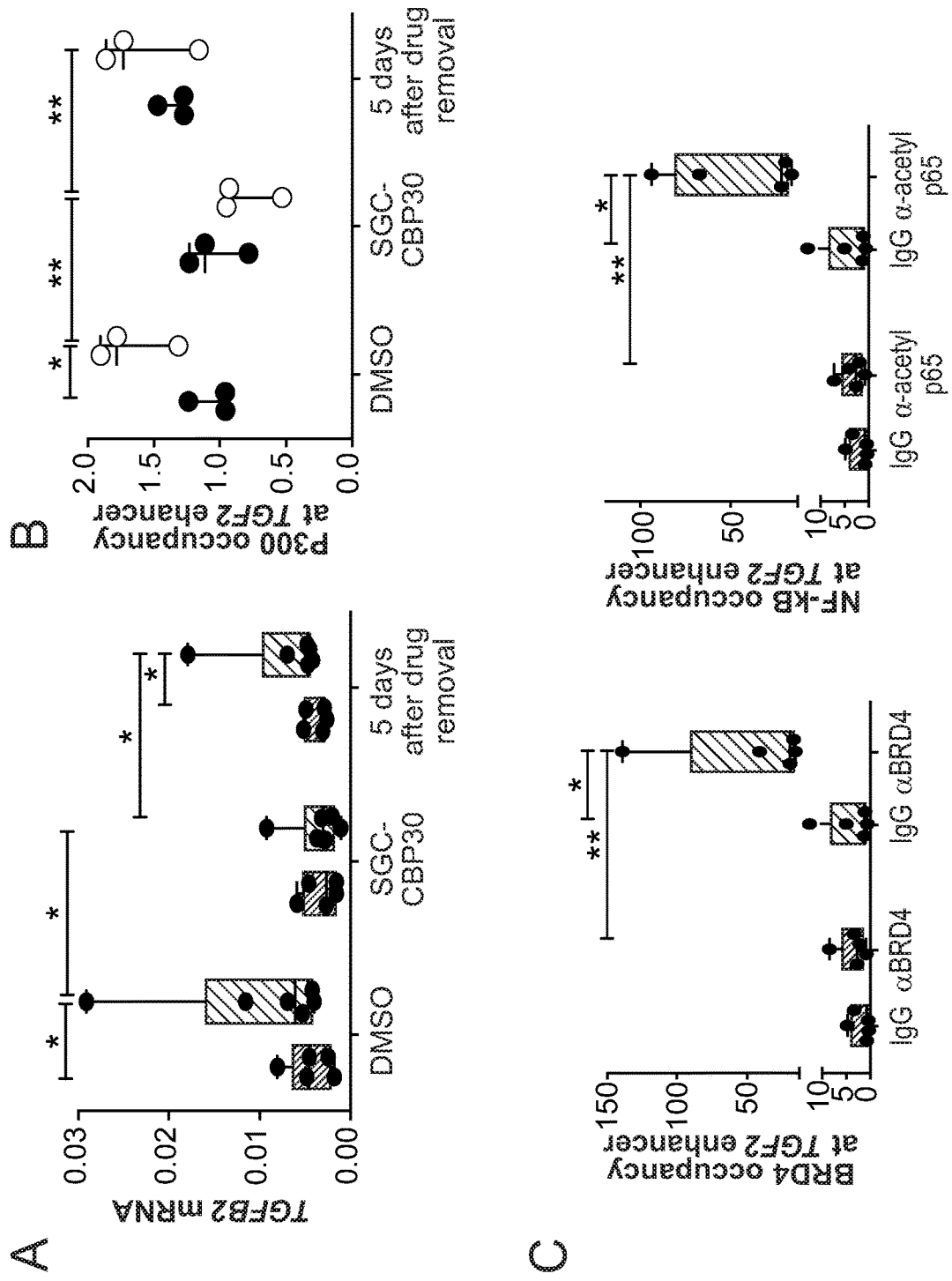

Third, pharmacological acetyltransferase inhibitors were used to support the role of enhancers in TGFβ2 expression and to identify therapeutic strategies for SSc. Bromodomain inhibitor SGC-CBP30 specifically suppresses the acetyltransferase activity of P300. It was found that 72 hours of SGC-CBP30 treatment normalized TGFβ2 expression in SSc fibroblasts to levels comparable to that of controls (FIG. 4A, P<0.05). Interestingly, TGFβ2 mRNA level rebounded back to 3-fold higher levels in SSc cells compared to control after drug removal, recapitulating steady-state differences. This indicated some form of epigenetic memory that re-activates the TGFβ2 enhancer in SSc fibroblasts. In support of this hypothesis, it was found by ChIP-qPCR that SSc fibroblasts re-establish high P300 occupancy at the TGFβ2 enhancer after drug removal (FIG. 4B).

The ability of SSc fibroblasts to re-establish high TGFβ2 expression after transient P300 inhibition was suggestive of super-enhancer priming that can be initiated by inflammatory effectors (e.g. NF-kB) and enforced by BRD4 recruitment (Brown J D et al. (2014). *Molecular Cell.* 56:219-231). In brief, BRD4 binds to acetylated histones and transcription factors to activate enhancers through further recruitment of RNA polymerase II and other transcription factors. In support of this hypothesis, increased NF-kB and BRD4 occupancy was found at the enhancer by ChIP-qPCR in SSc cells (FIG. 4C). Furthermore, high expression of TNFA (a potent inducer of NF-kB activity) was observed in SSc skin in situ (FIG. 8).

Figure 4D:
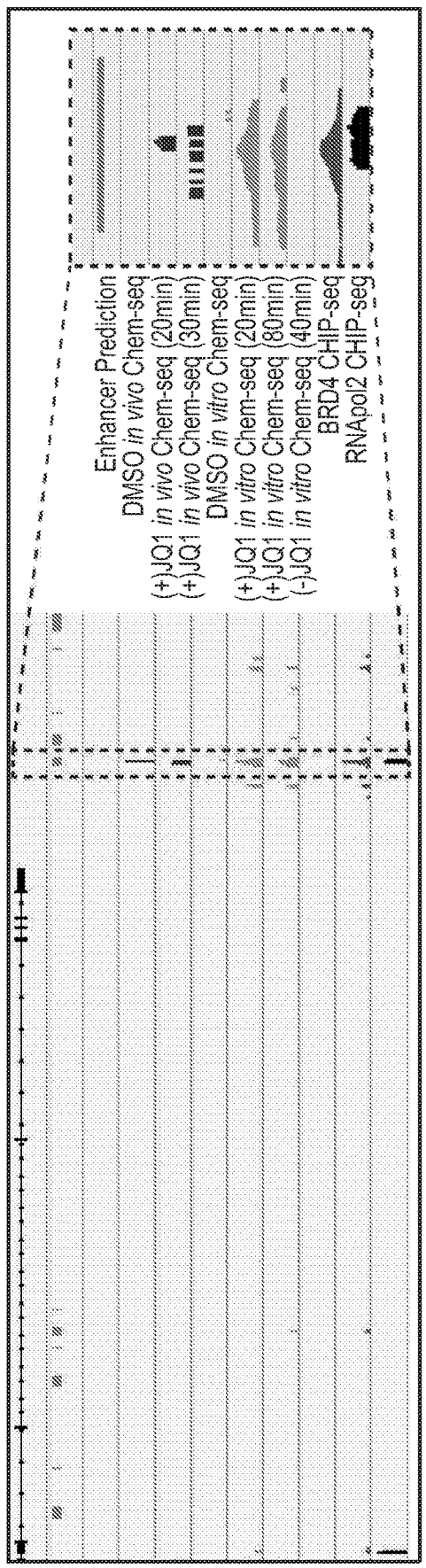
FIG. 4D: Chem-seq database reveals specific binding of JQ1, BRD4 and RNA polymerase at the TGFB2 enhancer (GSE44098, GSE43743). The negative enantiomer of JQ1 was used as a negative control.

These results were independently validated using a Chemseq database, which identifies genomic regions that are enriched upon pull-down of DNA-protein complexes that interact with the drug JQ1, a specific inhibitor of BRD4[17,18]. Strikingly, JQ1 specifically bound to the TGFB2 enhancer under consideration in this study, with direct overlap of CHIP-seq signals for BRD4 and RNA polymerase II (FIG. 4D).

Figures 4E, 4F:
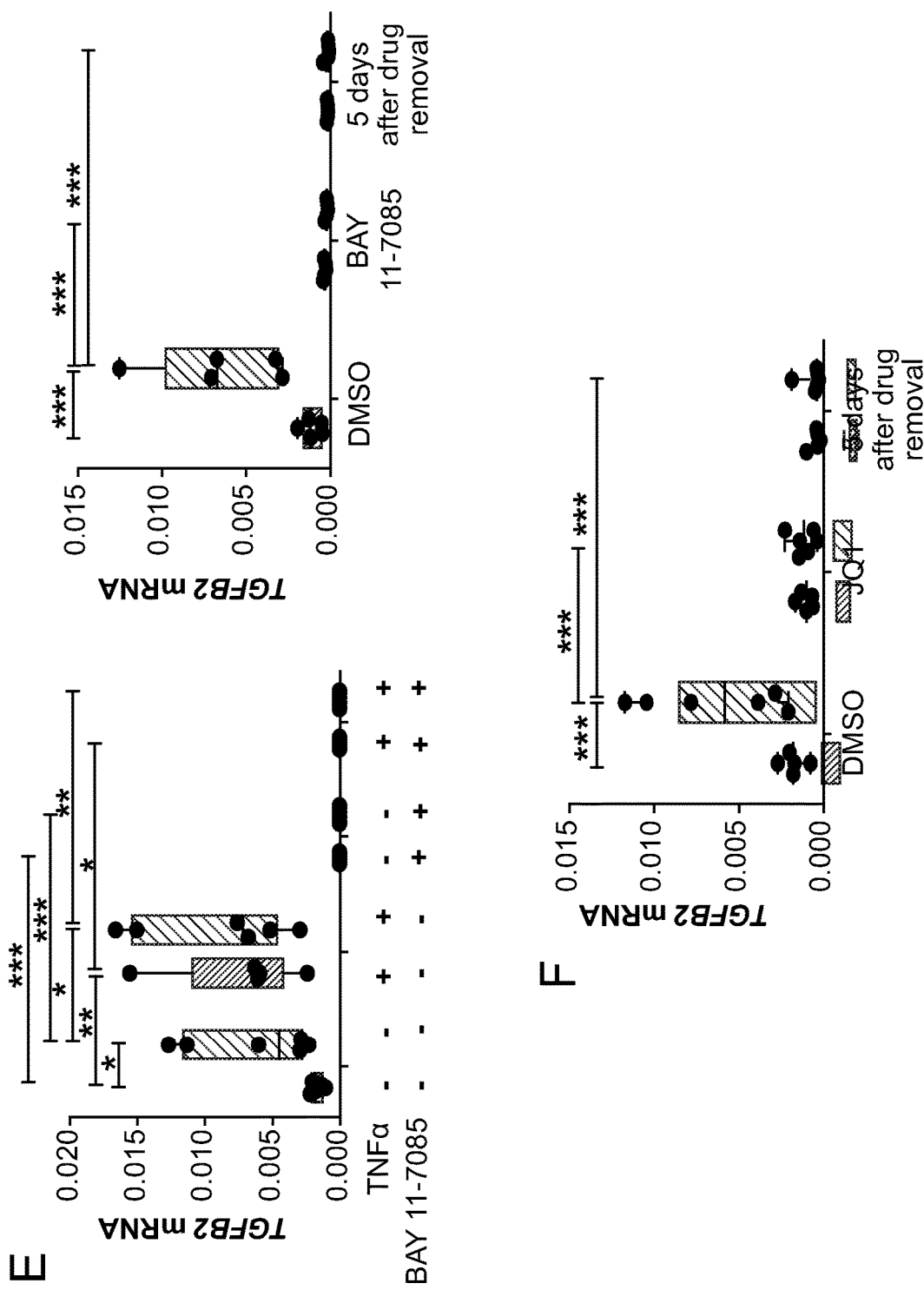
FIG. 4E: TNFα treatment induces TGFB2 mRNA expression in both control and patient cells. Co-treatment with TNFα and an NF-kB inhibitor (BAY 11-7085) prevents TGFB2 induction (left). NF-kB inhibition (72 hours) led to sustained normalization of TGFB2 expression in SSc fibroblasts even after drug removal (right).
In FIG. 4F BRD4 inhibition (JQ1, 72 hours) led to sustained suppression of TGFB2 expression in SSc fibroblasts even after drug removal.
Figures 4G, 4H, 4I:
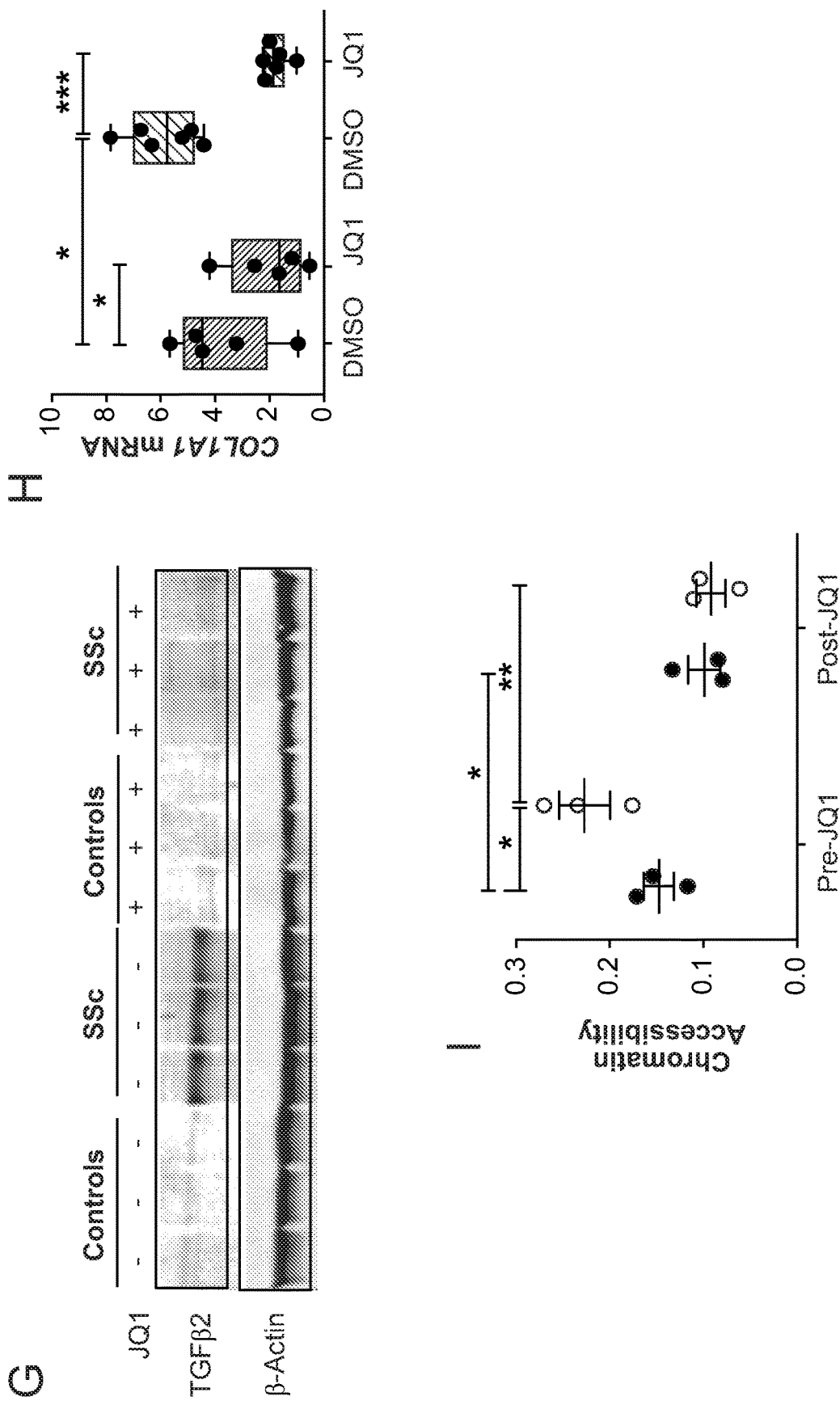
In FIGS. 4G and 4H, BRD4 inhibition with JQ1 normalizes TGFβ2 protein and collagen mRNA expression in SSc fibroblasts.
In FIGS. 4I, 4J and 4K, JQ1 treatment normalizes chromatin accessibility, H3K27ac and BRD4 occupancy at the TGFB2 enhancer in SSc fibroblasts. Values for CHIP-qPCR are displayed in percent input.
Figures 4J, 4K:
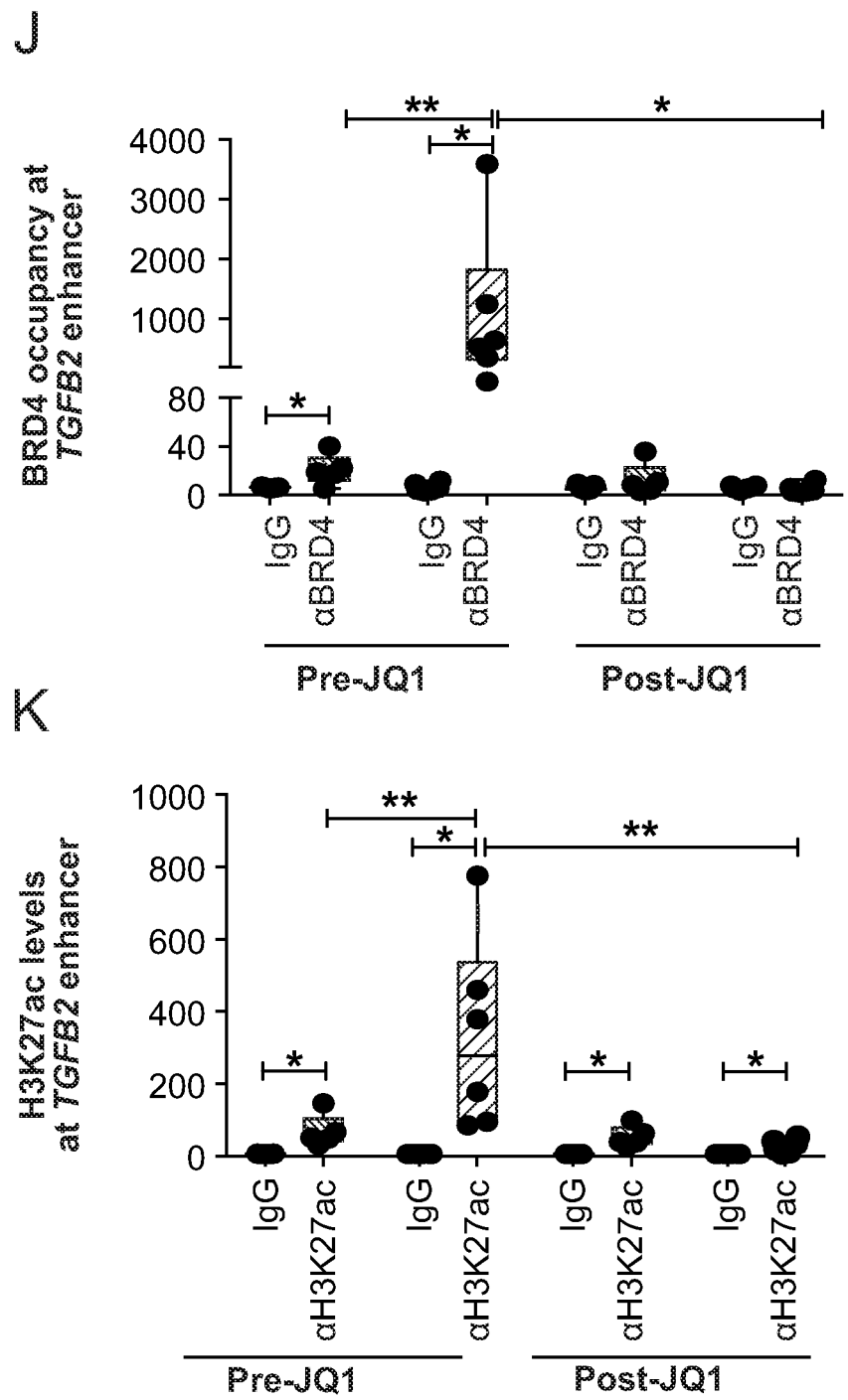
Figure 4L:
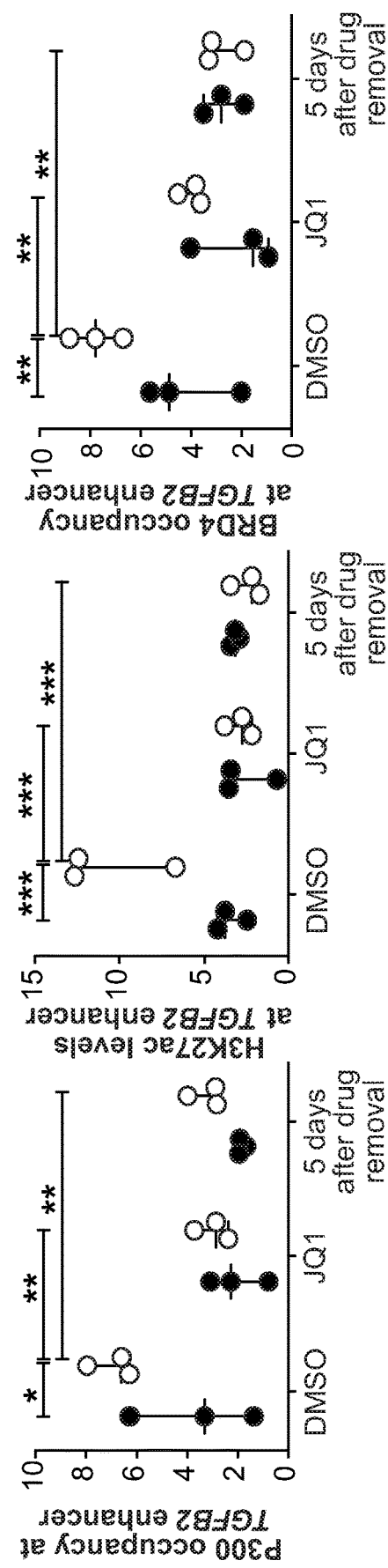
FIG. 4L, JQ1 treatment (72 hours) leads to sustained normalization of P300 and BRD4 occupancy and H3K27ac at the TGFB2 enhancer even after drug removal in SSc fibroblasts. Values for CHIP-qPCR are displayed in percent input.

If NF-κB partners with BRD4 to activate the TGFB2 enhancer, it was hypothesized that NF-kB activation would induce TGFβ2 expression, and that inhibition of NF-kB or BRD4 would decommission the TGFB2 enhancer in SSc fibroblasts. Indeed, stimulation with TNFα (a potent pro-inflammatory activator of NF-kB) increased TGFβ2 expression (FIG. 4E). Furthermore, a small molecule inhibitor of NF-κB (BAY 11-70585) robustly suppressed TGFβ2 expression in patient cells. Consistent with this hypothesis, treatment with the BRD4 inhibitor JQ1 rapidly normalized TGFβ2 mRNA and protein levels in addition to collagen expression in SSc fibroblasts Furthermore, a small molecule inhibitor of NF-kB (BAY 11-70585) robustly suppressed TGFβ2 expression in patient cells. Consistent with the hypothesis, treatment with the BRD4 inhibitor JQ1 rapidly normalized TGFβ2 mRNA and protein levels in addition to collagen expression in SSc fibroblasts (FIG. 4F, 4G, 4H). This occurred in association with complete normalization of BRD4 occupancy, H3K27ac and chromatin accessibility at the TGFB2 enhancer (FIG. 4I, 4J, 4K). Strikingly, unlike P300 inhibition, NF-κB or BRD4 inhibition achieved sustained repression of TGFB2 expression in patient cells even after removal of the drug (FIG. 4E, 4F). This occurred with continued normalization of BRD4 and P300 occupancy and H3K27ac modification of the TGFB2 enhancer in SSc fibroblasts after drug removal (FIG. 4L). These results demonstrated that NF-kB and BRD4 maintain epigenetic memory that re-activates the TGFβ2 enhancer in SSc fibroblasts.

Figure 4M:
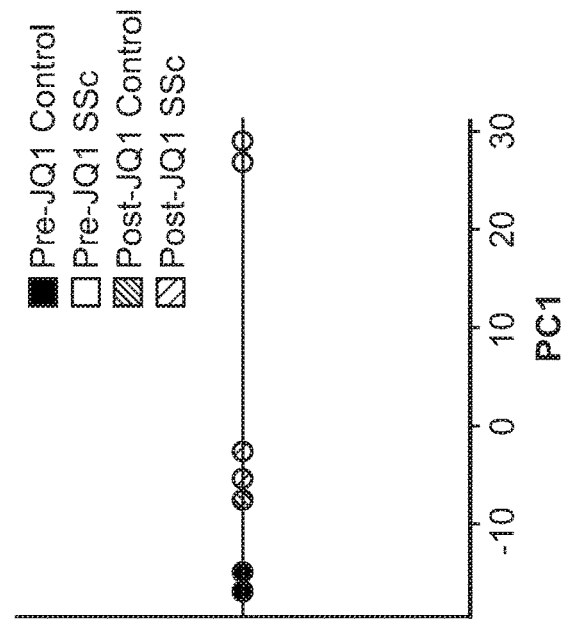
FIG. 4M: Heatmap of unsupervised hierarchical clustering of differentially expressed genes between vehicle or JQ1-treated control or SSc fibroblasts by RNA-seq (N=2). Rows represent differentially expressed genes between vehicle-treated control and SSc fibroblasts (FDR<0.05). Differences in expression of these genes are mitigated in SSc fibroblasts upon JQ1 treatment.
Figure 4N:
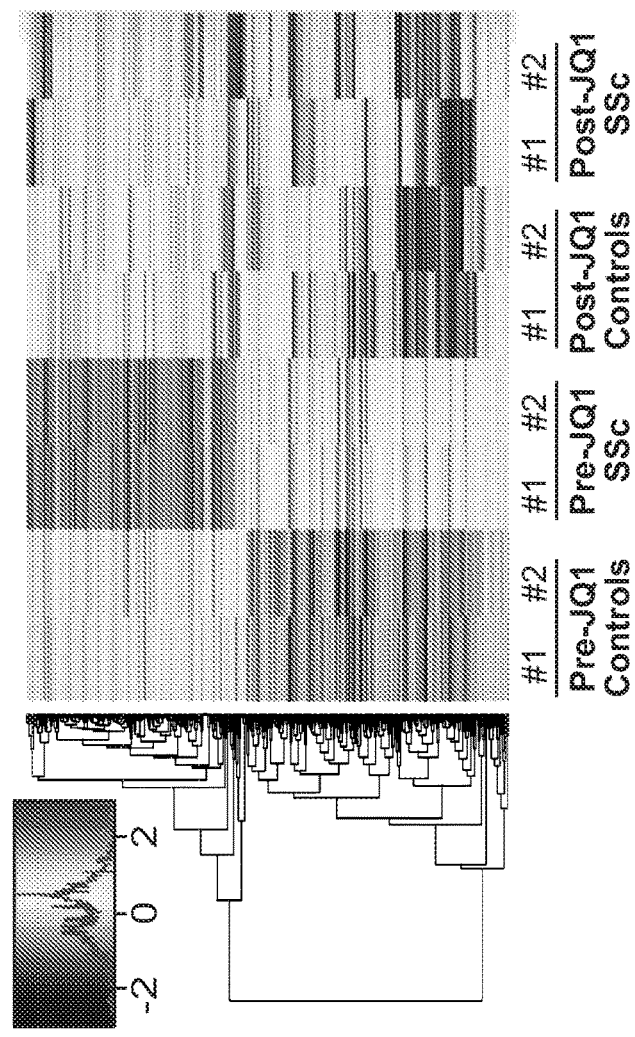

It was also hypothesized that BRD4 inhibition with consequent suppression of TGFβ2 expression would normalize the fibrotic synthetic repertoire of SSc fibroblasts. RNA-seq analysis confirmed that BRD4 inhibition significantly mitigated transcriptomic differences between control and SSc fibroblasts (FIG. 4M). Principal component analysis confirmed that JQ1 treatment causes SSc fibroblasts to cluster together with control samples in PC1 (67% of total variance; FIG. 4N). These results demonstrate that JQ1 attenuates differences in BRD4 occupancy, chromatin accessibility and pro-fibrotic gene expression in SSc fibroblasts.

Figures 7A, 7B:
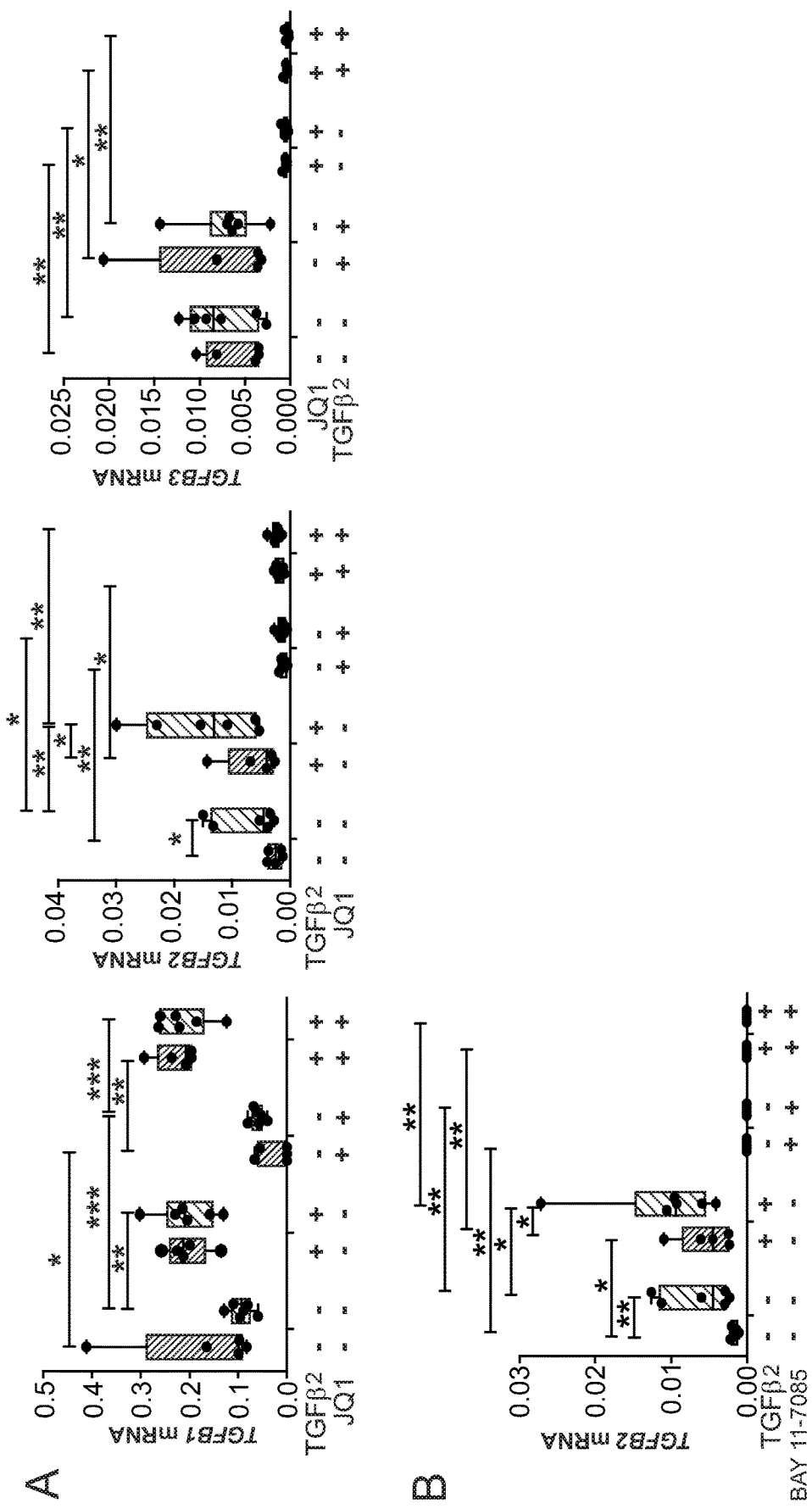
FIG. 7A: Control or SSc fibroblasts were cultured in the presence of DMSO, JQ1, TGFβ2 (long/mL), or both JQ1 and TGFβ2 (long/mL) for 48 hours, followed by RNA isolation and RT-qPCR.
FIG. 7B: Control or SSc fibroblasts were cultured in presence of DMSO, BAY 11-7085 (NF-kB inhibitor), TNFα or TGFβ2.

Since BRD4 is crucial in the activation of enhancers, it was hypothesized that BRD4 is mechanistically necessary for TGFβ2 expression. When SSc fibroblasts were treated with JQ1, TGFβ2 mRNA levels decreased. However, when JQ1-treated SSc fibroblasts were co-stimulated with TGFβ2 ligand for 24 hours, both control and SSc fibroblasts failed to induce TGFβ2 mRNA expression, demonstrating that BRD4 is involved in activating TGFβ2 expression (FIG. 7A). BRD4 recruitment was also involved in TGFβ3, but not for TGFβ1 induction. These results clearly demonstrate the BRD4 activity at enhancer 4514 is involved for TGFβ2 expression, and that targeted inhibition of BRD4 at enhancer 4514 specifically and sufficiently normalizes TGFβ2 expression in SSc fibroblasts.

Taken together, these results provide the first evidence for a specific enhancer that regulates the expression of TGFβ2 in primary human cells and that contributes to the pathogenesis of SSc. These data support the hypothesis that increased occupancy of P300 and BRD4 at Enhancer 4514 (Chr1: 218632917-218634115, hg19) is driving TGFβ2 expression, which in turn drives the expression of pro-fibrotic genes in SSc fibroblasts. Moreover, it was shown herein that modification of this open chromatin epigenetic mark, through pharmacological inhibition of histone acetyltransferases, is sufficient to transiently normalize TGFβ2 expression. JQ1 was also identified as a novel therapeutic drug for the treatment of Systemic Sclerosis. Specifically, it was found that JQ1 permanently normalizes TGFβ2 mRNA expression in SSc fibroblasts with a single 48 hr regiment through specific inhibition of BRD4 occupying enhancer 4514. The potential therapeutic efficacy of inhibiting NF-kB in Systemic Sclerosis was also demonstrated. Accordingly, agents that increase histone deacetylase activity, inhibit histone acetyltransferase activity or inhibit BRD4 activity at Enhancer 4514 will provide therapeutic benefit for scleroderma and other fibrotic diseases. The data also support the use of epigenetic marks at the TGFβ2 locus as biomarkers for disease predisposition, disease progression and therapeutic response in clinical trials. This scenario predicts failure of efforts to modify fibrosis through antagonism of αv integrin-mediated activation of TGFβ. While relevant to the activation of TGFβ1 or TGFβ3 (which contain integrin-binding RGE sequences), such a strategy would not influence TGFβ2 (which does not). It is also hypothesized that the elusive TGFβ2 activator may show coordinate upregulation in SSc fibroblasts, a hypothesis that will be tested through analyses of candidates that emerge from the RNA-Seq and ATAC-Seq profiles.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims, the invention can be practiced otherwise than as specifically described.

What is claimed is:

1. A method for treating a subject having or at risk of developing a transforming growth factor β2-associated disease, disorder and/or condition comprising:
    administering to the subject an effective amount of one or more agents that inhibit transforming growth factor β2 (TGFβ2) expression by inhibiting occupancy, of an enhancer sequence, by CBP/P300 and bromodomain-containing protein 4 (BRD4), wherein an inhibitor of CBP/P300 is selected from the group consisting of bromodomain inhibitor SGC-CBP30, C646, C375 and C146, and wherein the enhancer sequence is located 15 kb downstream of the TGFβ2 3'UTR, said transforming growth factor β2-associated disease, disorder and/or condition is Scleroderma and/or a fibrotic disease,
    thereby treating the subject.

2. The method of claim 1, wherein the one or more agents modulate activity of one or more molecules at the enhancer sequence and/or inhibit binding to the enhancer sequence and/or inactivate the enhancer functions and/or activities.

3. The method of claim 2, wherein the one or more agents: increase histone deacetylase activity, inhibit histone acetyltransferase activity, inhibit BRD4 activity or combinations thereof, as compared to a normal control at the enhancer sequence.

4. The method of claim 3, wherein the agent that inhibits acylation of a TGFβ2 enhancer sequence or promotes deacetylation of a TGFβ2 enhancer sequence is an inhibitor of CBP/P300.

5. The method of claim 1, wherein the agent that inhibits acylation of a TGFβ2 enhancer sequence or promotes deacetylation of a TGFβ2 enhancer sequence is a histone deacetylase (HDAC).

6. The method of claim 3, wherein an inhibitor of BRD4 is JQ1.

7. The method of claim 1, further comprising an agent that modulates NF-κB activity.

8. The method of claim 6, wherein the agent inhibits NF-κB activity.

9. The method of claim 1 wherein the subject has a transforming growth factor β2-associated disease, disorder and/or condition.

10. The method of claim 9, wherein a fibrotic synthetic repertoire (FSR) comprising one or more pro-fibrotic markers, is diagnostic of a transforming growth factor β2-associated disease, disorder and/or condition.

11. The method of claim 9, wherein an FSR comprises expression of one or more markers comprising COL1A1, SERPINH1 or combinations thereof, and/or TGFβ2 expression.

12. The method of claim 9, wherein the transforming growth factor β2-associated disease, disorder and/or condition is Scleroderma and/or a fibrotic disease.

* * * * *